United States Patent
Kohn et al.

(10) Patent No.: US 10,105,467 B2
(45) Date of Patent: Oct. 23, 2018

(54) BIOCOMPATIBLE POLYMER COMPOSITIONS FOR TISSUE VOID FILLING

(71) Applicant: Rutgers, The State University of New Jersey, New Brunswick, NJ (US)

(72) Inventors: Joachim B. Kohn, Piscataway, NJ (US); Atif J. Khan, Monroe, NJ (US); Nava Shpaisman, Kedumim (IL)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 97 days.

(21) Appl. No.: 14/762,636

(22) PCT Filed: Jan. 22, 2014

(86) PCT No.: PCT/US2014/012569
§ 371 (c)(1),
(2) Date: Jul. 22, 2015

(87) PCT Pub. No.: WO2014/116716
PCT Pub. Date: Jul. 31, 2014

(65) Prior Publication Data
US 2015/0335783 A1  Nov. 26, 2015

Related U.S. Application Data

(60) Provisional application No. 61/755,238, filed on Jan. 22, 2013.

(51) Int. Cl.
| | | |
|---|---|---|
| *A61L 27/18* | (2006.01) | |
| *A61L 27/54* | (2006.01) | |
| *A61L 27/58* | (2006.01) | |
| *A61M 31/00* | (2006.01) | |
| *A61N 5/10* | (2006.01) | |
| *A61B 6/00* | (2006.01) | |
| *A61K 31/138* | (2006.01) | |
| *A61L 27/56* | (2006.01) | |
| *A61K 47/10* | (2017.01) | |
| *A61K 9/00* | (2006.01) | |

(52) U.S. Cl.
CPC .............. *A61L 27/18* (2013.01); *A61B 6/481* (2013.01); *A61K 31/138* (2013.01); *A61L 27/54* (2013.01); *A61L 27/56* (2013.01); *A61L 27/58* (2013.01); *A61M 31/005* (2013.01); *A61N 5/1039* (2013.01); *A61K 9/0041* (2013.01); *A61K 47/10* (2013.01); *A61L 2300/216* (2013.01); *A61L 2300/404* (2013.01); *A61L 2300/41* (2013.01); *A61L 2300/416* (2013.01); *A61L 2300/436* (2013.01); *A61L 2300/604* (2013.01); *A61L 2430/34* (2013.01); *A61M 2210/1007* (2013.01); *Y10T 428/2982* (2015.01)

(58) Field of Classification Search
CPC combination set(s) only.
See application file for complete search history.

(56) References Cited

U.S. PATENT DOCUMENTS

| | | |
|---|---|---|
| 7,368,169 B2 | 5/2008 | Kohn et al. |
| 7,838,122 B2 | 11/2010 | Kohn et al. |
| 8,591,951 B2 | 11/2013 | Kohn et al. |
| 2005/0106119 A1 | 5/2005 | Brandom et al. |
| 2006/0013882 A1 | 1/2006 | Kohn et al. |
| 2009/0104254 A1 | 4/2009 | Sinko et al. |
| 2009/0317472 A1* | 12/2009 | Kohn .................... A61Q 15/00 424/486 |
| 2010/0021519 A1 | 1/2010 | Shenoy |
| 2012/0003177 A1 | 1/2012 | Shen et al. |
| 2013/0022569 A1 | 1/2013 | Uhrich et al. |

OTHER PUBLICATIONS

Azab et al., J. Controlled Release 123 (2007) 116-122.*
International Search Report and Written Opinion of the International Searching Authority dated May 19, 2014, issued in Application No. PCT/US2014/012569.
Shpaisman et al., "One-Step Synthesis of Biodegradable Curcumin-Derived Hydrogels as Potential Soft Tissue Fillers after Breast Cancer Surgery," Biomacromolecules, vol. 13, pp. 2279-2286, Jun. 16, 2012.

* cited by examiner

*Primary Examiner* — Robert S Cabral
(74) *Attorney, Agent, or Firm* — Fox Rothschild LLP

(57) ABSTRACT

Biodegradable, bioabsorbable cross-linked polymer tissue scaffolds for filling a void in human or animal soft tissue, such as a surgical or other wound, are disclosed. Drugs incorporated into the polymer backbone and/or loaded into the matrix are released directly to the target site. Additional non-toxic chemical constituents can be used to tune the hydrophilio hydrophobic and other physical properties of the cross-linked polymer tissue scaffolds, and incorporating brominated or iodinated constituents provides radio-opacity. The radio-opaque cross-linked polymer tissue scaffolds can assist in the targeting of radiation therapy.

21 Claims, 4 Drawing Sheets

BIOCOMPATIBLE POLYMER COMPOSITIONS FOR TISSUE VOID FILLING

CROSS-REFERENCE TO RELATED APPLICATION

The present application is the U.S. National Phase of International Patent Application Serial No. PCT/US14/12569, filed Jan. 22, 2014, which claims the benefit of priority under 35 U.S.C. § 119(e) of U.S. Provisional Application Ser. No. 61/755,238, filed Jan. 22, 2013. The entire disclosures of the applications noted above are incorporated herein by reference.

FIELD OF THE INVENTION

The invention is directed to cross-linked polymer tissue scaffolds and their use as soft tissue void-filling devices for post-surgical and other wound treatment, and for the treatment of various diseases post-surgery, including cancer.

BACKGROUND OF THE INVENTION

There continues to be a need for treatments for all types of wounds, including wounds created as part of a surgical procedure. In particular, when the injury involves the removal of tissue, thereby leaving a void in the tissue, it is frequently desirable to replace that removed tissue with a surrogate that will function structurally like the removed tissue, and ideally aid in regrowth of new healthy tissue during the healing process.

Examples of non-surgical wounds include battle wounds and wounds sustained in accidental injury and trauma. Examples of surgical wounds include wounds resulting from the removal of tumors, both cancerous and non-cancerous. One particular type of surgical cancer wound is a wound resulting from a lumpectomy, a procedure frequently performed in the treatment of breast cancer.

In 2010, over 209,000 new breast cancer cases were diagnosed in the United States, and a further 68,000 new Ductal Carcinoma In Situ (DCIS) cases were reported. DCIS is a type of mammary ductal carcinoma. Approximately 70% of these new cases were treated with breast conserving therapy (BCT), which generally consists of lumpectomy followed by radiation therapy. The radiation can be delivered to the entire breast (whole breast irradiation plus lumpectomy boost) or just to the lumpectomy cavity (Accelerated Partial Breast Irradiation, or APBI). APBI is frequently chosen as the front line treatment. Two modes of APBI are currently available, device-based and external beam radiation therapy (EBRT). Device-based therapy involves inserting a device into the lumpectomy cavity and is therefore not only invasive, but requires specialized physician expertise. Device-based APBI provides more conformal treatment than is possible with EBRT; that is, it is more focused and more conformed to the cavity, including the tissue that was previously in immediate contact with the removed breast lesion. In contrast EBRT is less focused and treats larger volumes, but has the advantages of being non-invasive (external beam) and requiring minimal additional physician training or expertise. Furthermore, even in the whole breast irradiation scenario, it is very common to deliver a boost dose to the lumpectomy bed. Thus accurately identifying and delimiting the lumpectomy cavity boundaries is critical for all patients receiving breast irradiation.

The utility and significance of the invention disclosed here can be illustrated by the fact that in the USA alone approximately 200,000 women are diagnosed with breast cancer each year, leading to over 40,000 breast cancer related deaths per year. Usually, a breast cancer is detected as a lump within the breast tissue. The most common initial form of treatment is a lumpectomy, i.e., the surgical removal of the lump. Thereafter, all subsequent medical interventions are designed to reduce the risk of local disease recurrence. This, however, is a significant challenge. Both radiation therapy and pharmaceutical treatment (chemotherapy) have severe toxic effects and are less than 100% effective in preventing local disease recurrence. As will be outlined in more detail below, the invention disclosed here addresses some of the challenges associated with the prevention of local disease recurrence.

Specifically, in the case of a lumpectomy, the surgical procedure is often followed by radiation therapy to ensure that all remaining cancer cells are eliminated from the lumpectomy cavity. There are different modes of radiation therapies, but in each case, a key challenge is to focus the beam of high-energy radiation into the area of the original lumpectomy cavity and to reduce the exposure of healthy tissue to radiation. While this sounds simple, the delineation of the lumpectomy cavity is a significant practical problem even among radiation oncology experts. Therefore, a radio-opaque (i.e., X-ray visible) tissue void filler that can facilitate the detection and localization of the lumpectomy cavity would be an important advance in the treatment of early breast cancer.

Chemotherapy is an alternative to radiation therapy. But, the treatment of patients with chemotherapeutic agents is not without risks and exposes the entire body of the patient to a significant toxic burden. A significantly improved approach would be to provide the local delivery of appropriate chemotherapeutic agents directly to the site of the lumpectomy. While this approach would not necessarily protect the patient from the development of metastatic disease outside of the breast, the local delivery of chemotherapeutic agents directly into the lumpectomy cavity could have significant health benefits for early breast cancer patients.

Identical considerations apply to a host of post-surgical cavities requiring post-operative void filling and image-characterization. These include post-craniotomy cavities in the brain, post-prostatectomy cavities in the pelvis, and post-operative cavities in the thorax/lung, and the abdomen.

BRIEF SUMMARY OF THE INVENTION

The present invention provides polymer tissue scaffolds based on biocompatible, bioabsorbable polymers for filling a void in human or animal soft tissue resulting from a surgical or non-surgical wound. The polymer compositions can be inherently radio-opaque and can include crosslinked or non-crosslinked polymers that contain biocompatible di- or triphenols as part of their backbone structure. Some of the polymers of the present invention include curcumin (a naturally occurring diphenol with proven anticancer properties) as part of their backbone structure. The combination of radio-opaque and hydrophobic di- or tri-phenolic monomers with hydrophilic monomers within the backbone of a polymer results in polymer compositions with excellent drug release properties, self-assembly properties and surfactant properties. These polymers can be formulated as self-assembled nanospheres with a diameter of about 30 to about 200 nanometer (as determined by laser light scattering measurements), as microbeads or macrobeads (i.e., microbeads have a diameter in the range of about 100 to about 500 micrometer and macrobeads have a diameter of about 0.501 to about 5 millimeter), or as crosslinked hydrogels, providing a wide range of polymer tissue scaffold formulations.

For each of these formulations a radio-opaque (i.e., X-ray visible) and corresponding radio-lucent (i.e., X-ray invisible) polymer tissue scaffold can be prepared. For each of these formulations, a corresponding drug-free or drug-loaded polymer tissue scaffold can also be prepared. The radio-opaque formulations have utility in targeting the boundaries of the cavity for radiation therapy, while the drug-loaded formulations provide a means to deliver chemotherapeutic agents or other drugs locally and directly to the surgical cavity. Finally, it is possible to prepare radio-opaque and drug-loaded formulations of polymer tissue scaffolds that act both as imaging agents for radiation therapy and as local drug delivery systems. The polymer compositions that contain curcumin will release biologically active curcumin during the process of polymer degradation and resorption. When these polymer tissue scaffolds are loaded with additional therapeutic agents such as chemotherapeutic drugs, angiogenic agents, drugs that promote wound healing and/or antibiotics, these agents will be released in the wound cavity in combination with curcumin. Specifically, when delivered in this fashion, the concomitant release of tamoxifen and curcumin was found to have significant synergistic effects.

The cross-linked polymer tissue scaffolds of the present invention are three-dimensional (3-D) cross-linked matrices of water-soluble polymers, which are characterized by a high moisture content. This high moisture content can mimic the water content of human tissue. The porosity of these 3-D matrices also allows the loading of drug molecules and their release from the cross-linked polymer tissue scaffolds. Cross-linked polymer tissue scaffolds as delivery vehicles are characterized by slow release of the drug at a high local concentration into the immediately surrounding tissues over an extended period of time.

A first aspect of the invention provides a nanosphere composition comprising the nanospheres described in U.S. Pat. No. 8,591,951, incorporated herein by reference in its entirety as if set forth herein, based on a single A-B-A triblock structure derived from water-soluble, hydrophilic and non-toxic "A" end blocks on each end and a hydrophobic "B" middle block of either a desaminotyrosyl-tyrosine polyarylate or poly-carbonate. According to one embodiment the desaminotyrosyl-tyrosines include the free acid (DTA) and acid esters (DTR). According to another embodiment the desaminotyrosyl-tyrosines consist of DTR's. According to yet another embodiment, the "B" middle block includes DTA and DTR's that are sufficiently iodinated, so that the nanospheres are radio-opaque.

The nanospheres are formulated within a biocompatible and generally recognized as safe (GRAS) injectable hydrogel such that the nanospheres comprise between 5 and 50% of the total volume of the nanosphere composition. Injectable hydrogels suitable for use with the nanospheres of the present invention are essentially conventional and can be readily identified by one having ordinary skill in the art without undue experimentation. Suitable hydrogels materials include, without limitation, those based on hyaluronic acid, alginate, collagen, gelatin, carrageenan, guar and poly(ethylene glycol).

The nanospheres made of radio-opaque diphenolic monomers are strongly radio-opaque by virtue of an appropriate degree of iodination. By virtue of being dispersed within the hydrogel, they render the entire hydrogel volume X-ray visible, while the hydrogel itself is radio-lucent. The hydrogel itself is pharmacologically inert and serves solely as the vehicle for the dispersion of the radio-opaque nanospheres.

Radio-opaque nanosphere-containing gel formulations according to the present invention can be placed into a surgical cavity or wound by a physician at the time of surgery, or can be injected percutaneously into an existing body cavity or void to delineate the position and size of the cavity or void for subsequent medical intervention such as radiation therapy. The present invention therefore also includes radiation therapy methods in which the radio-opaque nanosphere-containing gel formulations of the present invention are used to delineate a tissue a surgical cavity following tumor removal prior to radiation therapy. The placement can occur either by percutaneous injection or during surgery to fill the cavity.

The hydrogel and nanospheres are resorbable and can be designed to persist within the body cavity for predetermined periods of time. According to another embodiment the nanospheres can be loaded with drugs such as anti-infective agents, wound healing agents, chemotherapeutic agents, and the like, thereby providing additional utility for the nanosphere compositions. The present invention therefore further includes treatment methods in which therapeutically active agents are delivered to tissue defects to promote healing, prevent infection or deliver a chemotherapy drug.

The present invention therefore also provides nanosphere compositions that are radio-opaque and contain a chemotherapy agent. The compositions and treatment methods using the compositions have dual functionality: Delineation of position and size of the tissue cavity or void for targeting radiation therapy, and local delivery of pharmacologically or biologically active agents that prevent cancer recurrence. Agents can also be delivered that prevent infection, sensitize any remaining cancer cells to radiation, or support wound healing.

Another aspect of the present invention provides a composition comprising resorbable biocompatible polymers in the shape of elastic microbeads or microspheres (hereinafter referred to as microbeads) suspended in a pharmaceutically acceptable fluid (such as sterile isotonic saline solution), wherein the microbeads have a diameter of 100 to 500 micrometer, that can also be used to fill tissue defects. The concentration of the microbeads is as high as possible, limited solely by the need to maintain an injectable formulation. The microbeads are comprised of the specific bead-shaped polymer compositions disclosed previously in US Patent Publication No. US 2005/0106119, incorporated herein by reference in its entirety as if set forth herein, while selecting the above-disclosed size range that is larger than the beads disclosed as being useful for embolotherapy.

As with the nanosphere compositions of the present invention, microbead formulations according to the present invention include sufficiently iodinated polymers that are radio-opaque and can be injected percutaneously into an existing body cavity or void, or inserted during surgery, to delineate the position and size of the cavity or void for subsequent medical intervention such as radiation therapy. The present invention therefore also includes radiation therapy methods in which the radio-opaque microbead compositions of the present invention are used to delineate a surgical cavity following tumor removal prior to radiation therapy. The placement can occur either by percutaneous injection or during surgery to fill the cavity.

The microbeads are made of degradable polymers and by selecting appropriate compositions, the residence time of the microbeads in the tissue cavity or void can be tuned for predetermined periods of time with preferred embodiments persisting from several weeks to several months. According to another embodiment, as with the nanospheres of the present invention, the microbeads of the present invention can be loaded with drugs such as anti-infective agents, wound healing agents, chemotherapeutic agents, and the like, thereby providing additional utility for the microbead compositions. The present invention therefore further includes treatment methods in which therapeutically active agents are delivered to tissue defects to promote healing, prevent infection or deliver a chemotherapy drug.

The present invention thus also provides microbead compositions that are radio-opaque and contain a chemotherapy agent. The microbead compositions and treatment methods using the compositions therefore also can have dual functionality: Delineation of position and size of the tissue cavity or void for targeting radiation therapy, and local delivery of pharmacologically or biologically active agents that prevent cancer recurrence. Agents can also be delivered that prevent infection, sensitize any remaining cancer cells to radiation, or support wound healing.

A third embodiment of the invention provides a soft tissue void filler comprising a preformed hydrogel made of the biodegradable, bioadsorbable crosslinked polymer tissue scaffold composition prepared from di- or tri-phenols as the hydrophobic monomers and hydrophilic blocks of poly (alkylene oxide)s, which are polymerized together as polycarbomnates or dicarboxylic acid polyarylates. A preferred composition uses DTA and DTR diphenols as one of the hydrophobic monomers and curcumin as the second hydrophobic component and poly(ethylene glycol) as the hydrophilic component in such a way that curcumin is both part of the polymer backbone and the site of chain crosslinks.

According to one embodiment, the DTA, DTR and curcumin monomers are sufficiently iodinated to render the composition radio-opaque. These preformed hydrogels have mechanical properties that can be adjusted to match the properties of human soft tissues, the iodinated, tyrosine-derived diphenols render the entire volume of the hydrogel X-ray visible, and upon degradation of the gel, biologically active curcumin is liberated and released into the tissue cavity or void over prolonged periods of time. Curcumin has known antibacterial, anti-inflammatory, and anticancer properties. In another embodiment based on the same hydrogel formulation, additional drugs can be loaded into the hydrogel, resulting in a formulation that simultaneously fulfills two requirements: (1) it delineates the position and size of the tissue cavity or void and (2) it releases curcumin and optionally a second drug into the tissue cavity or void to enhance wound healing or reduce the local recurrence of cancer within the tissue cavity or void. This embodiment of the invention is designed to be placed into a tissue cavity or void at the time of a surgical procedure and before the tissue cavity or void is closed by the surgeon.

One embodiment of the invention provides soft tissue void fillers without a drug component. The void filler comprises a biodegradable, bioabsorbable cross-linked polymer tissue scaffold composition prepared from cross-linked polymers of diphenols (hydrophobic monomers) and hydrophilic monomers.

According to one embodiment of the invention, the diphenols are selected from desaminotyrosyl tyrosine free acid (DTA) and/or esters (DTR). The hydrophilic monomers preferably comprise poly(alkylene glycol)s, such as poly (ethylene glycol)s (PEGs), poly(propylene glycol)s or poly (butylene glycol)s, particularly those having a weight-average molecular weight range of about 1 to 5 kDalton.

Applicants have now discovered that by varying the proportion of hydrophobic to hydrophilic monomers, the structural properties of the resulting cross-linked polymer tissue scaffolds can be engineered so that the physical properties of tissue can be mimicked when filling a wound cavity resulting from a non-surgical injury or a surgical procedure. For example, the physical properties of breast tissue can be mimicked when filling a cavity resulting from a lumpectomy. In this way, the cross-linked polymer acts as a 3-D void-filling device that prevents tissue collapse and serves as a scaffold for tissue regeneration. When cross-linked with cross-linking agents, such as dihydrazides, the polymers show angiogenic properties, thereby further promoting blood flow and tissue regeneration. Other bifunctional cross-linking compounds can be used to cross-link the polymers, and/or polymers can be selected that inter-molecularly cross-link.

Another embodiment of the invention provides soft tissue void fillers as above, further comprising a drug component. The drug or drugs can be incorporated into the polymer backbones, or loaded into the 3-D matrix. For example, phenolic drugs can be incorporated into the polymer backbones, vide infra. When a drug is loaded into the 3-D matrix, it need not be the same diphenol. Further, the drug need not even be a diphenol, but can be selected from other chemical classes, including without limitation, chemotherapeutic agents, angiogenic agents, antibiotics and other drugs that promote wound healing. Still further, drugs may be both incorporated into the polymer backbone and loaded into the matrix, thereby providing a biodegradable, bioabsorbable cross-linked polymer tissue scaffold capable of releasing drugs directly into the soft tissue void at different rates, depending on whether the drug is incorporated into the polymer backbone or loaded into the matrix, vide infra.

Another embodiment of the invention provides soft tissue void fillers as above, with or without a drug component, that have been rendered radio-opaque by sufficient heavy atom (bromine or iodine) substitution of the phenol aromatic rings. Iodine substitution is preferred, more preferably two iodine atoms per halogenated aromatic ring. When used to fill a tissue cavity, the radio-opaque cross-linked polymer tissue scaffold functions as a marker of the soft-tissue void boundaries for external beam radiation therapy. One application would be for irradiation of a lumpectomy cavity following breast cancer surgery.

Additional embodiments of the invention include methods of wound treatment and methods of cancer treatment, in which a gap or void in soft tissue, for example the void remaining following a lumpectomy in a breast cancer patient, is filled with one of the above-disclosed cross-linked polymer tissue scaffold compositions selected to provide void filling, drug delivery, radio-opacity or combinations thereof.

changes in the freezing point of the water encapsulated in the pores of 50CUR50PEG and 25CUR50DTE25PEG cross-linked polymer tissue scaffolds, after reaching the maximum swelling (T=0) and after incubation at 37° C. in PBS for 5 weeks.

Figure 4:
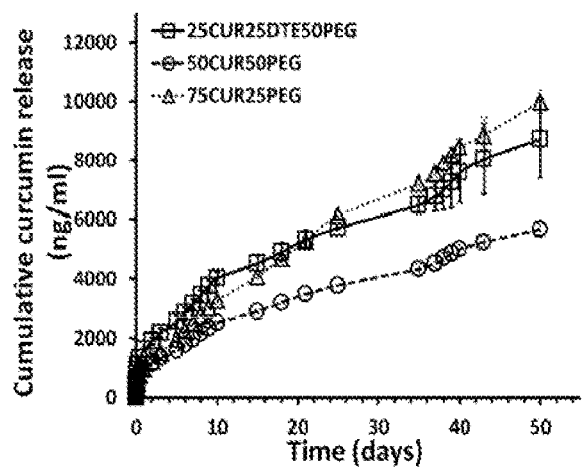

FIG. 4 displays the cumulative release profile of curcumin and curcumin conjugates from the curcumin-derived cross-linked polymer tissue scaffolds over 50 days.

Figure 5:
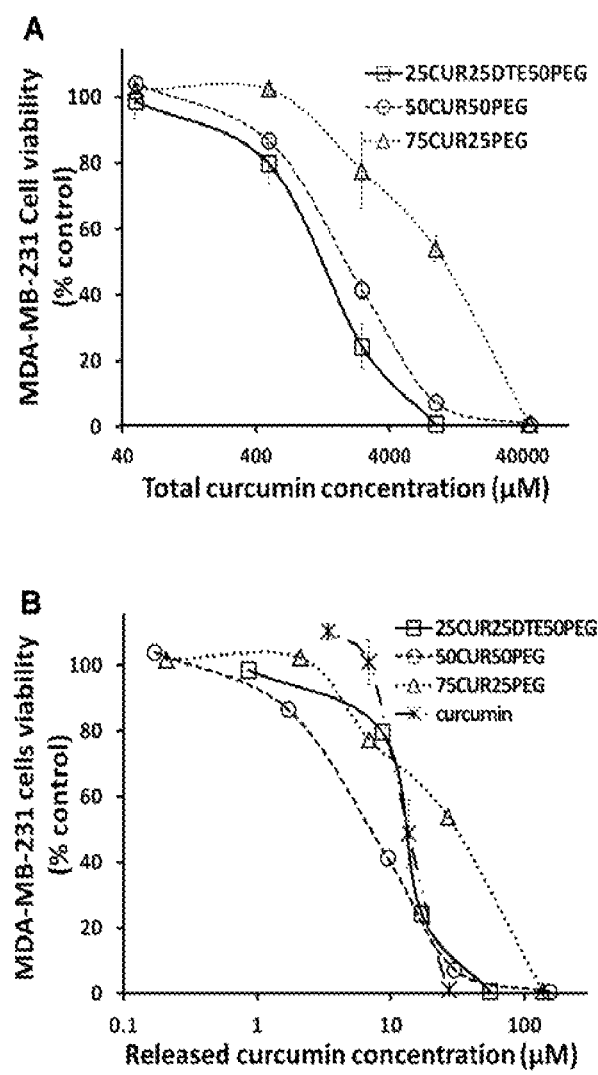

FIG. 5 shows graphs of the cytotoxicity of curcumin-derived cross-linked polymer tissue scaffolds to MDA-MB-231 breast cancer cells. (A) MDA-MB-231 cells were treated for 6 days with various curucmin-derived cross-linked polymer tissue scaffolds with total curcumin concentration of 50 to 45,000 µM. (B) Cytotoxicity of curcumin and curcumin-derived cross-linked polymer tissue scaffolds using values of released curcumin extrapolated from the release profile of each scaffold as reported in FIG. 4.

Figure 6:
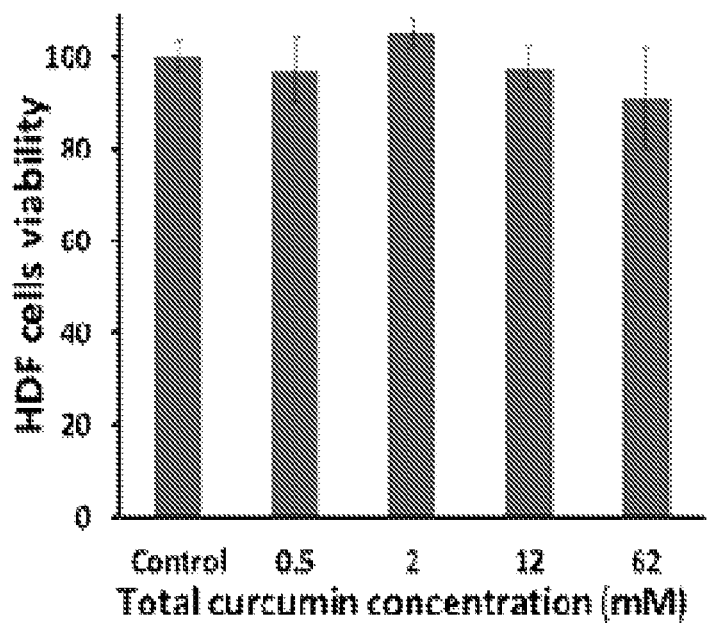

FIG. 6 depicts the cytotoxicity of 0.5 to 62 mM 50CUR50PEG on confluent HDF cells.

DETAILED DESCRIPTION OF PREFERRED EMBODIMENTS

Definitions

The term "GPC" stands for the analytical chemical method known as gel permeation chromatography.

The term "PBS" stands for phosphate buffered saline.

The term "HDF" stands for human dermal fibroblasts.

The term "drug" refers to a pharmaceutically active compound or agent which is useful in the diagnosis, treatment, or prevention of disease or abnormal condition, or the treatment of the symptoms of a disease or abnormal condition.

The term "DTA" stands for desaminotyrosyl tyrosine free acid. The term "DTR" stands for desaminotyrosyl tyrosine esters. Suitable esters include, without limitation, benzyl, ethyl, butyl, hexyl, octyl, decyl and dodecyl esters. The term "DTE" stands for desaminotyrosyl-tyrosine ethyl ester, DTH is the hexyl ester, DTO is the octyl ester, etc.

One embodiment of the present invention is directed to a biodegradable, bioabsorbable cross-linked polymer tissue scaffold composition for filling a void in human or animal soft tissue, which composition comprises cross-linked polymers of biocompatible hydrophobic and hydrophilic monomers. In one embodiment, the hydrophobic and hydrophilic monomers are present in a molar ratio between about 25:75 and about 75:25. In another embodiment, the molar ratio of hydrophobic monomers to hydrophilic monomers is between about 50:50 to about 75:25, and in more preferred embodiment, about 50:50, vide infra. In a preferred embodiment, the hydrophobic monomers are diphenol monomers.

Cross-linked polymer compositions are prepared by the methods disclosed, for example, by U.S. Pat. Nos. 7,368,169 and 7,838,122, in which polycarbonate, polyarylate or poly-iminocarbonate copolymers of desaminotyrosyl-tyrosine are cross-linked with dihydrazides of water-soluble polymers, including a dihydrazide of poly(ethylene glycol). However, the present invention is directed to compositions in which desaminotyrosyl-tyrosine and/or diphenolic drug molecules (as hydrophobic monomers) are incorporated into the polymer backbone together with hydrophilic monomers, such as poly(alkylene oxides). Further, the same or different drug molecules can be loaded into the matrix to assist in achieving the desired wound-healing activity. The entire disclosures of U.S. Pat. Nos. 7,368,169 and 7,838,122 are incorporated herein by reference as if set forth herein.

The hydrophobic monomers, for example diphenol monomers, can further comprise one or more groups selected from the group consisting of carboxylic acid esters and carboxylic acids. The molar fraction of diphenol monomers carrying carboxylic ester or acid groups determines the degree of cross-linking of the polymer (vide infra), with the molar fraction preferably ranging between about 10% and about 100% and the cross link density preferably ranging between about 8% and about 80%, and more preferably the molar fraction ranging between about 30% and about 80% and the cross link density ranging between about 25% and about 75%.

The soft tissue void-filling cross-linked polymer tissue scaffold comprises an implantable, degradable polymer that is either radio-opaque or radio-transparent, depending on whether brominated/iodinated hydrophobic monomers are incorporated. For radio-opacity, iodine substitution is preferred, more preferably 2 iodine atoms per halogenated aromatic ring. The cross-linked polymer tissue scaffold serves as a 3-D void filler that prevents tissue collapse and serves as a scaffold for tissue regeneration in a surgical or non-surgical wound cavity. In one specific embodiment the biocompatible hydrophobic monomers comprise diphenols, either iodinated or non-iodinated. The hydrophilic monomers preferably comprise poly(alkylene glycols), more preferably poly(ethylene glycols).

The hydrophobic monomers are preferably diphenols, which may comprise phenolic drugs which are released in vivo as the cross-linked polymer tissue scaffold biodegrades. Examples of suitable diphenolic drugs include without limitation, curcumin, quercetin, anthocyanidin, luteolin and catechin, so that the inventive polymers comprise these moieties as part of the polymer backbone. Further, the hydrophobic monomers can include structural or radio-opaque compounds such as DTA, DTE, and the iodinated counterparts, $I_2$DTA and $I_2$DTE. When the phenols comprise iodine-substituted aromatic rings, these moieties are present in an amount effective to render the polymer radio-opaque. The cross-linked polymer tissue scaffold can comprise any combination of drug, structural and radio-opaque hydrophobic monomers.

Hydrophilic monomers suitable for use with the present invention are selected from water-soluble polymer blocks with a weight-average molecular weight between about 100 and about 10,000, examples of which include, but are not limited to water-soluble polysaccharides, poly(vinyl alcohols), poly(N-methylpyrrolidones), poly(ethyloxazolines), polyamines, poly(amino-amides), poly-peptides, poly(alkylene oxides), cellulosics such as carboxy-methylcellulose and hydroxyethyl-cellulose, chondroitin sulfate, heparin, alginates, and proteins such as collagen or gelatin. Typically, the weight-average molecular weight of the water-soluble polymer blocks ranges between about 250 and about 5000 Daltons, and more typically between about 500 and about 3000. In one embodiment the weight-average molecular weight of the water-soluble polymer blocks ranges between about 1000 and about 2000 Daltons.

A preferred water-soluble polymer is a poly(alkylene oxide), with poly(ethylene glycol) (PEG) being a preferred poly(alkylene oxide). PEG, when used, preferably has a weight-average molecular weight between about 500 and about 3000 Daltons, more preferably between about 750 and about 1500, and still more preferably between about 1000 and about 1250 Daltons. In one preferred embodiment, the PEG has a weight-average molecular weight of about 1000 Daltons (1 kDalton).

The polymers can be any type of polymer within the confines of the description above, polymerized as polycarbonates or dicarboxylic acid polyarylates, but are preferably poly-carbonates.

One aspect of the invention is directed to tailoring the chemical (degree of cross-linking, degradation rate), physical (stiffness, swelling, radio-opacity and water uptake), and biological (anticancer) properties of the diphenol drug-derived cross-linked polymer tissue scaffolds by tuning the molar ratio of the polymer's monomeric units. As an example, three potential clinical benefits can be associated with the use of cross-linked polymer tissue scaffolds in conjunction with localized soft-tissue cancers: (a) the cross-linked polymer tissue scaffolds act as a 3-dimensional void filler that prevents tissue collapse, and also serve as a scaffold for tissue regeneration in the tumor cavity; (b) inherent radio-opacity will provide easier targeting for radiation therapy; and (c) the cross-linked polymer tissue scaffolds can provide localized, controlled release of the anticancer agent directly into the affected site.

The inventive cross-linked polymer tissue scaffold properties desired for a void-filling composition, including the chemical (degradation rate), physical (stiffness, swelling, radio-opacity and water uptake), and biological (anticancer, antibiotic, etc.) properties are achieved by tuning the molar ratio of the polymer's monomeric units. Thus, the molar ratio of the sum of the hydrophobic diphenolic monomers versus the sum of the hydrophilic monomers should lie in the range between about 25:75 to about 75:25. Preferably, the ratio of diphenolic monomers to hydrophilic monomers is between about 50:50 to about 75:25. More preferably, the ratio of poly-phenolic monomers to hydrophilic monomers is about 50:50. The sum of the diphenolic monomers includes both the diphenolic drug monomers and any other diphenolic monomers which might be present. For example, both 50CUR50PEG and 25CUR25DTE50PEG contain 50 mole percent of diphenolic monomers, and 25CUR50DTE25PEG and 75CUR25PEG contain 75 mole percent of diphenolic monomers.

The cross-linked polymer tissue scaffolds can further comprise an additional drug or pharmaceutically active agent loaded into the matrix. That is, the additional drug is not covalently attached to the polymer as part of the polymer backbone. Such additional drugs can include anti-tumor drugs, for example, cisplatin, paclitaxel, tamoxifen, or any of the other known chemotherapy agents listed in Table 3. Anti-tumor drugs commonly used in the treatment of breast cancer include doxorubicin, cyclophosphamide, fluorouracil, paclitaxel, docetaxol, carboplatin, cisplatin, ifosphamide, vincristine, etoposide, all of which can be loaded into the inventive cross-linked polymer tissue scaffolds. Other classes of additional drugs for loading into the matrix include, without limitation, angiogenesis agents, antibiotics, and other drugs that promote wound healing.

According to one aspect of the invention, cross-linked polymer tissue scaffolds according to the present invention are prepared by cross-linking biocompatible polymers with a difunctional cross-linking compound. One embodiment provided by this aspect of the present invention is formed by cross-linking polymers of diphenol drugs and hydrophilic monomers. Another embodiment provided by this aspect of the present invention is formed by cross-linking polymers of diphenol drugs, desaminotyrosyl-tyrosine and hydrophilic monomers. When the cross-linking agent is a dihydrazide, an angiogenic composition is formed. Other bifunctional cross-linking compounds can be used to cross-link the polymers, and/or polymers can be selected that inter-molecularly cross-link. For the purposes of the present invention, cross-linking moieties include, without limitation, molecules with double bonds (e.g., acrylic acid derivatives), which can be attached to the pendent carboxylic acid groups for cross-linking to increase the strength of the polymers.

With such cross-linked polymers the resulting tissue scaffolds show angiogenic properties, which can accelerate wound healing and formation of tissue. The soft cross-linked polymer tissue scaffold consists of a network of interconnected pores that facilitate tissue ingrowth and the rapid formation of a vascular network. Data in subcutaneous implantation in a rat model illustrate rapid tissue ingrowth and angiogenesis.

When angiogenesis-promoting properties are not essential, the polymers of the inventive cross-linked polymer tissue scaffold can be cross-linked with essentially any difunctional compound capable of reacting with the polymer to cross-link the polymer and form a cross-linked polymer tissue scaffold. See, for example, U.S. Patent Application Publication No. 2009-0104254, the disclosure of which is incorporated by reference. Furthermore, U.S. Pat. No. 7,368,169 discloses polymers with pendant free carboxylic acid groups, which can be cross-linked with diamines, diols, amino-alcohols, and the like; essentially any bifunctional compounds with functional groups that will react with carboxylic acid groups. An important variable of the present invention, in addition to the molar quantity of hydrophilic monomer, such as poly(ethylene glycol), is the molar fraction of diphenol monomers with pendant carboxylic acid groups, which determines the cross-link density and thereby the mechanical properties and degradation profile of the cross-linked polymer tissue scaffold. In order to achieve a balance of appropriate properties in the cross-linked polymer tissue scaffold, the mole fraction of diphenol monomers carrying carboxylic ester or acid groups is between about 10% and about 100% and the cross link density range is between about 8% and about 80%, and preferably the molar fraction is between about 30% and about 80% and the cross link density range is between about 25% and about 75%.

Further, another drug can be loaded into the pores of the 3-D matrix. The drug can be the same as, or different from the backbone-incorporated diphenol drug. This loading can be accomplished by conventional means, for example, by having the drug present in situ during polymerization and cross-linked polymer tissue scaffold formation. The drug can also be loaded into the pores of the matrix using an appropriate solvent. For example, tamoxifen can be loaded into a curcumin-derived matrix using a swelling method, which comprises treating the polymer with a solution of tamoxifen in dichloromethane, evaporating of the solvent, washing with methanol to remove surface (unbound) tamoxifen, and hydration of the tamoxifen-loaded polymer to form the cross-linked polymer tissue scaffold. This method provides excellent loading efficiency (87-91%), with high loadings (5-40 weight %) of incorporated tamoxifen.

Accordingly, depending on the therapeutic need, the cross-linked polymer tissue scaffolds can contain, either within the polymer backbone or loaded into the pores of the matrix, one or more pharmaceutically active agents.

Further, the cross-linked polymer composition can be optimized for formation of soft, elastic macrobeads/macrospheres of cross-linked polymer, which when injected through a needle, will fill any irregularly shaped tissue cavity. The macrobeads are spherical particles 0.501 millimeter up to 5 millimeter in diameter, preferably between 0.501 and 2 millimeter, and more preferably between 1 and 2 millimeter in diameter. Macrobeads between 1 and 2 millimeter in diameter fill a size range that can still be injected percutaneously with a large gauge needle, but these beads can also just be placed into the wound by a surgeon. The size of the macrobeads can be controlled during the manufacturing process, directly from the polymerization mixture. The porosity of the macrobeads can also be controlled. Macrobeads being ejected from a narrow gauge needle show excellent compressibility and recover their shape. This embodiment of the invention provides an alternative to injectable gels as void-filling agents. As already noted, the polymers can be made radio-opaque or radio-transparent, and their biodegradation rate is tunable. Further, the macrobeads can be dried if desired.

Macrobeads of the invention can also be used to define the void for subsequent medical treatment, such as targeted radiation. Thus, the macrobeads can be used as lumpectomy cavity markers for radiation therapy.

The cross-linked polymer tissue scaffold consists of a network of interconnected pores that facilitate tissue ingrowth and the rapid formation of a vascular network. Further, the inherent radio-opacity of the iodinated variants provides easier targeting of external beam radiation therapy of the void boundaries in cavities resulting from surgical removal of tissue, such as a lumpectomy. Thus, in one embodiment of the invention, a void in breast tissue following a lumpectomy is filled with a cross-linked polymer tissue scaffold composition of the invention, either radio-opaque or radio-transparent. The cross-linked polymer tissue scaffold for lumpectomy void filling can also comprise an anti-tumor drug which is effective to prevent the growth or metastasis of the tumor cells removed by the lumpectomy.

The polymer tissue scaffolds of the present invention have broad utility for the treatment of wounds, both surgical and non-surgical. Thus, the drug to be either incorporated into the polymer backbone or loaded into the cross-linked polymer tissue scaffold can be selected for the therapeutic need presented by the wound. Diphenols according to the present invention, therefore, include diphenolic drugs. Any drug having two or more phenolic hydroxyl groups is a candidate for incorporation into the backbone polymer structure. Examples of such diphenolic drugs include, without limitation, curcumin, quercetin, anthocyanidin, luteolin and catechin. In one preferred embodiment, the diphenolic drug comprises curcumin. Due to the biological activities of curcumin, the soft tissue void fillers comprising this drug have anti-cancer, anti-bacterial and anti-inflammatory properties.

An example of a soft tissue void-filling embodiment with multiple drug components for treatment of lumpectomy cavities following breast cancer surgery is a curcumin-derived cross-linked polymer tissue scaffold loaded with tamoxifen, which possesses the following advantages:

(a) All building blocks (DTR, curcumin, poly(ethylene glycol)) are natural food ingredients, metabolites or GRAS (generally recognized as safe) materials.

(b) The cross-linked polymer tissue scaffold can be prepared as either radio-opaque or radio-transparent, depending on the incorporation of either DTR or $I_2$DTR.

(c) The cross-linked polymer tissue scaffold will bioresorb, and the resorption time can be varied over a wide range by appropriate selection of the components of the polymer.

(d) The mechanical properties of the cross-linked polymer tissue scaffold resemble those of healthy breast tissue.

(e) Random degradation of the cross-linked polymer tissue scaffold leads to slow, sustained release of water-soluble prodrugs of curcumin (curcumin-PEG conjugates) that are cytotoxic to cancer cells but non-cytotoxic to confluent HDF cells. Stable release of curcumin is observed over more than 80 days. Concurrently, tamoxifen is released in a diffusion-controlled process relatively rapidly from the 3-D matrix at a near-zero order rate for up to one month.

(f) As discussed above, when cross-linked with cross-linking agents such as dihydrazides, the cross-linked polymer tissue scaffolds show angiogenic properties, thereby further promoting blood flow to, and tissue regeneration in the treated region. Other bifunctional cross-linking compounds can be used to cross-link the polymers, and/or polymers can be selected that inter-molecularly cross-link, as demonstrated the Examples.

Curcumin, a diphenol derived from the plant turmeric (*Curcuma longa*), which is commonly used as a spice component, has shown a wide range of biological and pharmacological activities. Recently, curcumin was found to have anti-proliferative and pro-apoptotic effects against diverse soft tissue tumors in vitro and in vivo, particularly as a carcinogenesis suppressor of prostate, colon, brain and breast cancers. The effects of curcumin on cancers has been linked to its inhibitory effects on various transcription factors, including proximal activating-protein-1 (AP-1), nuclear factor kappaB (NF-kB), as well as causing diminished expression and activity of several matrix metalloproteinases. Remarkably, curcumin has been proven to be safe, even at very high doses, in various animal and human studies. However, in spite of its efficacy and safety, curcumin's low bioavailability and physiological instability hamper its therapeutic utility. Ongoing efforts have been focused on bioavailability and aqueous (physiological) solubility, which includes synthesis of stable analogues, and encapsulation of the curcumin into nanoparticles, liposomes or micelles. As discovered herein the water solubility of curcumin can be increased by synthesizing polycurcumin (polyester) in which the curcumin is incorporated into a polyester polymer backbone together with water-soluble monomers.

A one-step synthesis of curcumin-derived cross-linked polymer tissue scaffolds is described in Example 1A. In this composition, curcumin is part of the backbone as well as a site of cross-linking. Incorporation of curcumin into the backbone leads to precise control of high curcumin content and to protection of curcumin from degradation, leading to the release of active curcumin upon degradation. The cross-linked polymer tissue scaffold's physical properties are similar to human tissue. The release of curcumin can be adjusted to a targeted medical application by changing the mole ratio of the polymer building blocks. Because 50CUR50PEG has a controllable long time curcumin release profile, selective cytotoxicity against cancer cells and mechanical properties similar to breast tissue, this particular composition can be used as a bioactive void filler for excised cancerous breast tissue while also suppressing and killing breast cancer cells in the vicinity of the implant.

Therefore, one embodiment of the present invention provides biodegradable curcumin-derived cross-linked polymer tissue scaffolds that are useful in breast cancer therapy as post-lumpectomy implants. The therapeutic properties of curcumin also make such cross-linked polymer tissue scaffolds suitable for treatment of other surgical or non-surgical wounds. In one design, a biodegradable carbonate linkage is used to both incorporate curcumin into the polymer backbone as a monomer unit and to form cross-links between curcumin molecules. All of the curcumin monomer's hydroxyl groups are blocked in the resultant polymer, thereby providing protection of curcumin from oxidation and metabolic degradation. In this design, simultaneous drug release and clearance of the cross-linked polymer tissue scaffold from the body are achieved upon hydrolysis of the backbone linkages.

At least two types of curcumin-derived cross-linked polymer tissue scaffolds can be formed by one-step poly-condensation of curcumin in the presence of triphosgene to form degradable carbonate linkages: (i) cross-linked polymer tissue scaffolds which include the water-soluble poly(ethylene glycol) (PEG) and (ii) cross-linked polymer tissue scaffolds which include both PEG and desaminotyrosyl-tyrosine esters (DTR) and/or the iodinated analog, $I_2DTR$. DTR is a derivative of a naturally occurring tyrosine dipeptide. The DTR component is used to adjust the hydrophobicity of the final cross-linked polymer tissue scaffold and $I_2DTR$ is used to provide radio-opaque behavior. Hydrophobicity can be modulated both by the amount of DTR monomer in the polymer backbone and the carbon content of the ester chain, R. The free acid analog, DTA, can also be incorporated to reduce hydrophobicity, increase degradation rate and provide additional cross-linking sites on the polymer backbone.

The present invention also provides compositions comprising nanospheres based on a single A-B-A triblock structure derived from water-soluble, hydrophilic and non-toxic "A" end blocks on each end and a hydrophobic "B" middle block of either a desaminotyrosyl-tyrosine polyarylate or polycarbonate. According to one embodiment the desaminotyrosyl-tyrosines include the free acid (DTA) and acid esters (DTR). According to another embodiment the desaminotyrosyl-tyrosines consist of DTR's. According to yet another embodiment, the "B" middle block includes DTA and DTR's that are sufficiently iodinated, so that the nanospheres are radio-opaque.

The nanospheres are formulated within a biocompatible and generally recognized as safe (GRAS) injectable hydrogel such that the nanospheres comprise between about 5 and about 50%, typically between about 10 and about 40%, and more typically between about 20 and about 30% of the total volume of the nanosphere composition. Injectable hydrogels are essentially conventional and can be identified by one of ordinary skill in the art without undue experimentation. Suitable hydrogel materials include, without limitation, those based on hyaluronic acid, alginate, collagen, gelatin, carrageenan, guar and poly(ethylene glycol).

The triblock structures are derived from water-soluble, hydrophilic, and non-toxic end blocks and a hydrophobic middle block of either a polyarylate or polycarbonate. Thus, according to one specific aspect of the present invention, nanospheres of a triblock A-B-A structure are provided wherein each A end block is a water-soluble, hydrophilic and non-toxic polymer or oligomer; and the middle B block is a hydrophobic polymer or oligomer with the same or different repeating units having a structure according to Formula I:

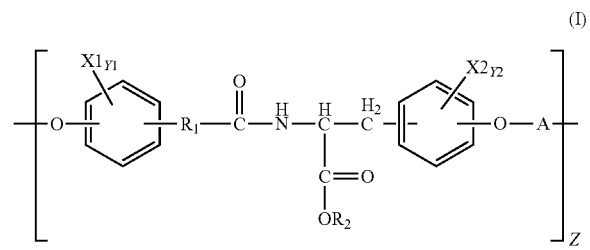

wherein X1 and X2 are independently I or Br; Y1 and Y2 are independently 0, 1 or 2; Y1+Y2=0, 1, 2, 3 or 4; A is —C(C=O)—R—C(=O)— or —C(=O)—; Z is between 2 and about 100, inclusive; $R_1$ is CH=CH or $(CH_2)_n$— wherein n is from 0 to 18, inclusive; alternatively $R_1$ is —X—$(CH_2)_i$—, where i is an integer selected from 1 through 4, and X is oxygen (O), sulfur (S) or $NR^4$, where $R^4$ is selected from the group consisting of hydrogen, and alkyl containing from 1 to 6 carbon atoms; $R_2$ is selected from hydrogen, and straight and branched alkyl, alkoxyalkyl and arylalkyl groups containing up to 18 carbon atoms; and R is selected from a bond or straight or branched alkylene, alkoxylene, alkylarylene and alkoxyarylene groups containing up to 18 carbon atoms.

The end blocks are preferably poly(alkylene oxides) having the structure of:

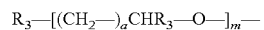

wherein m for each A is independently selected to provide a molecular weight for each A between about 1000 and about 15,000 g/mol; $R_3$ for each A and within each A is independently selected from hydrogen and lower alkyl groups containing from one to four carbon atoms; and a is an integer greater than or equal to one. In a preferred embodiment, the end blocks have the structure $CH_3O$—$[CH_2CH_2O$—$]_m$.

The triblock structures self-assemble spontaneously to form biocompatible, bio-degradable nanospheres, which are then dispersed in the injectable hydrogel. Nanosphere compositions according to the present invention are radio-opaque when one or more hydrogens of a sufficient number of aromatic rings of the Formula I structure have been replaced with an iodine or bromine atom. Radio-opaque compositions serve as markers for imaging tissue voids filled with the compositions, which has utility in targeting radiation therapy.

The spontaneous self-assembly of the triblock structure can be used to complex drugs or other active ingredients useful for treatment of the tissue void, such as anti-tumor agents, antibiotics, antimicrobials, peptides, proteins, oligonucleotides (e.g., siRNA's), hormones, i.e., essentially any useful pharmaceutical or biological agent in the broadest sense, and provide a means for the prolonged release of the complexed materials. The present invention therefore also includes injectable delivery systems for biologically and pharmaceutically active compounds formed by complexing an active compound with the nanospheres by the technique disclosed in U.S. Pat. No. 8,591,951 and then dispersing the nanosphere complex in a hydrogel carrier suitable for injection.

The present invention also provides microbeads formed from polymers comprising one or more units described by Formula II:

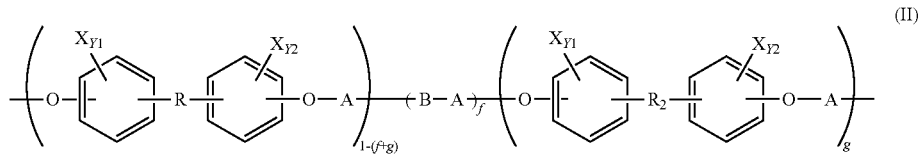

(II)

wherein X=I or Br; Y1 and Y2 can independently=0, 1, 2, 3 or 4;

wherein f is between 0 and less than 1; g is between 0 and 1, inclusive; and f+g is between 0 and 1, inclusive;

wherein A is selected from the group consisting of:

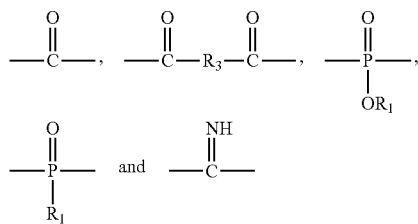

wherein $R_1$ is independently an H or an alkyl group ranging from 1 to about 18 carbon atoms containing from 0 to 5 heteroatoms selected from O and N;

wherein $R_3$ is a saturated or unsaturated, substituted or unsubstituted alkylene, arylene, or alkylarylene group containing up to about 18 carbon atoms and 0 to 8 heteroatoms selected from O and N;

wherein B is an aliphatic linear or branched diol or a poly(alkylene glycol) unit; and wherein R and $R_2$ are independently selected from:

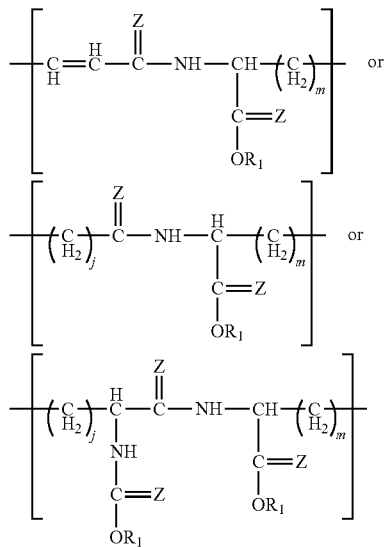

wherein for each $R_2$, each subgroup $R_1$ is hydrogen, and for each R, each subgroup $R_1$ is independently a long chain aliphatic hydrocarbon;

wherein j and m are independently integers from 1 to 8 inclusive; and wherein Z is independently either O or S.

In preferred variations to Formula II, f is greater than 0.1 to about 0.3. Preferably, f is greater than 0.2 to about 0.25. In other preferred variations to Formula II, g is greater than 0.1 to about 0.35. More preferably, g is greater than 0.2 to about 0.3.

In a preferred variation to Formula II, B is a poly($C_1$-$C_4$ alkylene glycol) unit present in a weight fraction of less than about 75 wt %. In other preferred variations, the poly (alkylene glycol) unit is a poly($C_1$-$C_4$ alkylene glycol) present in a weight fraction is less than about 25 wt %.

Typically, B is a poly(alkylene glycol) unit having a molecular weight of about 10,000 Daltons or less, and more typically, about 4000 Daltons or less. B is preferably a poly(ethylene glycol) unit having a molecular weight between about 1000 and about 2000 Daltons.

Microbeads of the polymers are typically prepared by adding a dilute solution (about 5 wt %) of polymer in a solvent for the polymer, such as dimethyl sulfoxide (DMSO), through a narrow gauge needle to a volume of water containing an appropriate surfactant. The needle gauge selected will determine the polymer particle size. The precipitated polymer spheres are isolated by filtration through a drop funnel and permitted to air dry, followed by cryogenic grinding and drying under vacuum at an elevated temperature selected to prevent the formation of agglomerates (about 50° C.). The microbeads are then suspended in a pharmaceutically acceptable fluid (such as sterile isotonic saline solution), wherein the microbeads have a diameter of about 100 to about 500 micrometer, and preferably between about 200 and about 400 micrometer, which can also be used to fill tissue defects. There is a lower limit of about 100 micrometer to how small the microbeads can be in order not to trigger an immune response or an inflammatory response, or otherwise be rapidly absorbed into tissues. The concentration of the microbeads in the pharmaceutically acceptable fluid is as high as possible, limited solely by the need to maintain an injectable formulation.

Microbeads according to the present invention are also radio-opaque when one or more hydrogens of a sufficient number of aromatic rings of the Formula II structure have been replaced with an iodine or bromine atom. Radio-opaque microbeads likewise have utility as markers for imaging tissue voids for targeting radiation therapy.

Therapeutic agents can be incorporated onto the microbeads on at least one region of the surface, or in some cases in the product, thereby providing local release of such agents. In some preferred embodiments, the therapeutic agent is delivered from a thin polymer coating or other carrier on the particle surface. In another preferred variation, the therapeutic agent is delivered by means of a polymer coating. In other preferred embodiments of the microbeads, the therapeutic agent is delivered from at least one region or one surface of the microbeads. In other preferred embodiments of the microbeads, the therapeutic agent is contained within the microbeads as the agent is blended with the polymer or admixed by other means known to those skilled in the art. In other preferred embodiments, the therapeutic agent can be chemically bonded to a polymer or other carrier used to coat the particles and/or bonded to at least one portion of the particle polymer and/or bonded to the particle polymer indirectly by means of a separate linker or ligand. In another variation, the microbeads may comprise more than one therapeutic agent, for example, coated on at least a portion of the particle surface, admixed within the polymeric matrix, etc.

By the foregoing methods, drugs or other active ingredients useful for treatment of the tissue void, such as anti-tumor agents, antibiotics, antimicrobials, peptides, proteins, oligo-nucleotides, hormones, i.e., essentially any useful pharmaceutical or biological agent in the broadest sense, can be loaded in or on the microbead and provide a means for the prolonged release of the materials within the tissue void. The present invention therefore also includes injectable delivery systems for biologically and pharmaceutically active compounds prepared by the techniques disclosed in US Patent Publication No. US 2005/0106119.

A further embodiment of the invention is a method of targeting radiation therapy following a lumpectomy, comprising filling a void in breast tissue following a lumpectomy with one of the inventive radio-opaque compositions. Another embodiment of the invention is a method of targeting a lumpectomy cavity for radiation therapy, comprising filling the lumpectomy cavity with one of the radio-opaque compositions of the present invention, imaging the cavity, and irradiating the imaged cavity at the boundaries of the imaged radio-opaque composition.

When the compositions of the present invention are used as void fillers for the cavity resulting from removal of a cancerous tumor, such as a lumpectomy cavity, the compositions can contain one or more chemotherapeutic drugs. While breast cancer is used as a specific example, the compositions can be used to treat any cavity remaining following the removal of a cancerous tumor, in which case the chemotherapeutic agent will be selected for its efficacy against the type of tumor removed. For example, compositions of the present invention containing an appropriate chemotherapy drug can be used to treat the cavity remaining following surgical removal of a glioblastoma. An agent or agents can be selected to kill any remaining tumor cells or to prevent their metastasis, or both. Examples of suitable anti-tumor agents are listed in Table 3. Agents can also be used that inhibit the metastasis of any remaining tumor cells, or which sensitize tumor cells to radiation therapy.

Still yet another embodiment provides compositions that are radio-opaque and contain a chemotherapy agent. The compositions and treatment methods using the compositions have dual functionality: Delineation of position and size of the tissue cavity or void for targeting radiation therapy, and local delivery of pharmacologically or biologically active agents that prevent cancer recurrence. Agents can also be delivered that prevent infection, sensitize any remaining cancer cells to radiation, or support wound healing.

Those cancers for which treatment involves surgery, and where a post-surgical void is formed, can be suitable for treatment with the compositions of the present invention. Such cancers include, without limitation:

Anal Cancer
Gastrointestinal Carcinoid Tumors (includes Appendix cancer)
Brain Tumor
Skin Cancer
Bladder Cancer
Bone Cancer
Ewing Sarcoma Family of Tumors
Spinal Cord Tumors
Breast Cancer
Bronchial Tumors
Cervical Cancer
Colon Cancer
Rectal Cancer
Esophageal Cancer (stent)
Extracranial Germ Cell Tumors
Melanoma
Gastric Cancer
Soft Tissue Sarcoma
Head & Neck Cancer
Throat Cancer
Aids Related Cancers
Kidney Cancer (used to replace tissue around the kidneys removed if necessary)
Langerhans Cell Histiocytosis
Lip & Oral Cancer
Lung Cancer
Liver Cancer
Mesothelioma
Neuroblastoma
Pheochromocytoma (surrounding tissue removal)
Paraganglioma
Parathyroid Cancer
Penile Cancer
Pituitary Tumor
Pleuropulmonary Blastoma
Prostate Cancer (surrounding tissue)
Transitional Cell Cancer
Rhabdomyosarcoma
Sarcoma
Thymoma Carcinoma
Thymic Carcinoma
Thyroid Cancer
Urethral Cancer
Uterine Sarcoma
Vaginal Cancer
Vulva Cancer
Wilms Tumors The compositions of the present invention possess numerous advantages for surgical and non-surgical wound treatment in general, and cancer treatment in particular, more particularly breast cancer treatment.

Lumpectomies are performed through curvilinear incisions after which two surgical flaps are raised and the volume of interest is exposed. The lesion is removed en bloc and the cavity walls are visually examined for hemostasis and for visible abnormalities. The wound is then closed in layers with absorbable sutures. The compositions can be inserted in several ways. In one embodiment, the crosslinked polymer scaffolds are provided as prepackaged macrobeads of spherical shape (e.g., 0.501 to 5 millimeter), which can easily be packed into the cavity prior to closure. Alternatively, the crosslinked polymer scaffolds may be presented to the clinician in the form of a larger slab that can be cut to a size and shape that fits into the anticipated void. Chemotherapy drugs to be delivered by the crosslinked polymer scaffold can be incorporated into the polymer backbone or loaded into the pores of the hydrogel matrix.

Alternatively, small spheres of the crosslinked polymer scaffold, or the nanosphere or microbead compositions of the present invention containing a suitable anti-tumor agent can be loaded into a large, e.g., Toomey tip, syringe (with a large bore plastic end) and then injected into the cavity as a final step before the final closing skin/subcutaneous suture. Alternatively, the device may be inserted after a lumpectomy in a surgeon or physician's office (a "closed cavity" insertion). In this embodiment, the lumpectomy cavity is visualized on ultrasound and using sterile biopsy techniques, an injecting device is inserted through the skin and into the lumpectomy cavity. The seroma is drained and the composition is delivered percutaneously into the surgical void. Similar techniques can be applied in a variety of postoperative cavities including but not limited to postoperative craniotomy cavities, postoperative sarcoma beds, and postoperative prostatectomy and thorax/abdomen voids. Using similar embodiments, the compositions of the present invention can be deployed to pack and fill traumatic or post-traumatic surgical voids.

Similarly, radiotherapy is routinely indicated after a prostatectomy when the surgical specimen demonstrates positive margins, extra-capsular extension or seminal vesicle involvement. Identifying the extent of the prostatectomy bed can be difficult postoperatively. The radio-opaque compositions according to the present invention can be positioned in the prostatectomy bed to indicate position for postoperative radiotherapy. Similarly, postoperative sarcoma and melanoma beds can be obscured after plastic reconstruction to close the wound. The radio-opaque compositions according to the present invention can be positioned in the plane of the resection bed to localize the at-risk volume and to deliver therapeutics.

A further embodiment of the invention is directed to cosmetic surgery, in particular touch-up cosmetic surgery where the inventive compositions can be used to fill voids, gaps or the areas around implants. Such areas can be smoothed over to achieve cosmetic acceptability. In this way the inventive compositions can be used as cosmetic agents, in addition to their utility for wound and disease treatment. A further cosmetic utility includes tissue augmentation, such as minor breast augmentation.

The invention is further illustrated by the following Examples, which are not intended to limit the scope of the invention in any way.

EXAMPLES

Materials and Methods

Materials

Desaminotyrosyl-tyrosine esters (DTR) were synthesized according to known procedures, including the ethyl ester (DTE). 98% pure curcumin was purchased from Chroma-Dex™ (USA). Bis(trichloro-methyl) carbonate (triphosgene) and poly(ethylene glycol) Mw-1000 kD (PEG1k) were obtained from Fluka (USA). N,N-dimethylformamide (DMF) was obtained from EMD (Germany). Pyridine, dichloromethane (DCM), Hexane and isopropyl alcohol (IPA) were obtained from Fisher Scientific (USA). Deuterated chloroform ($CDCl_3$), trifluoroacetic acid (TFA), Dulbecco's phosphate buffered saline (PBS), Tween 80, N-acetylcysteine, and butylated hydroxytoluene (BHT) were obtained from Sigma-Aldrich Chemical Co. (USA). Fetal bovine serum (FBS) was obtained from Atlanta Biologicals (USA), Dulbecco's modified eagle medium (DMEM) and Gentamicin were obtained from Invitrogen (USA). Alamar blue metabolic assay was obtained from AbD Serotec (USA).

Methods

Example 1A. Synthesis of Curcumin-Derived Cross-Linked Polymer Tissue Scaffolds

Figure 1:
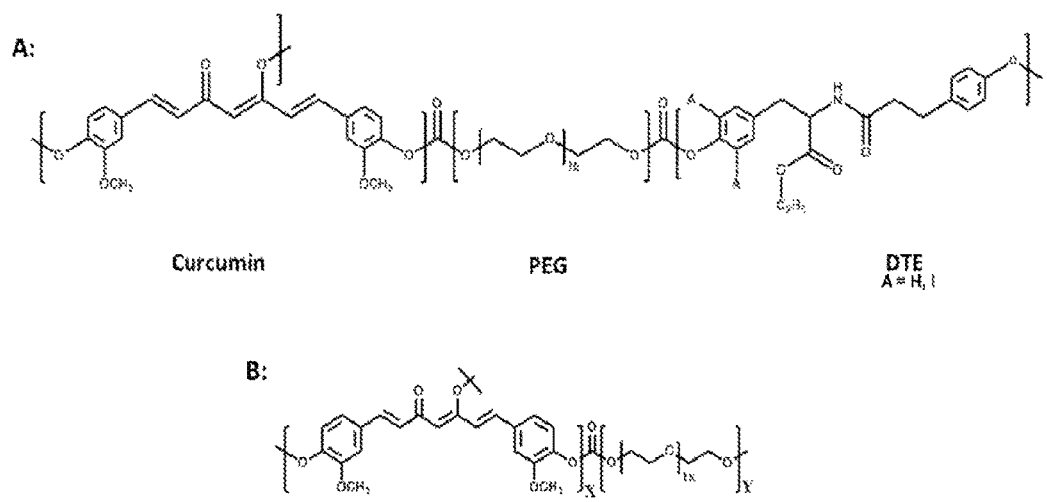
FIG. 1 displays the chemical structures of the repeat units of curcumin-derived cross-linked polymer tissue scaffolds composed of curcumin, PEG1k and DTE (A=H or I) (A); and curcumin and PEG1k (B).

Five types of curcumin-derived cross-linked polymer tissue scaffolds (FIG. 1) were synthesized following the general procedure as summarized in Table 1. A mixture of curcumin (1.84 g, 5 mmol), PEG1k (5 g, 5 mmol) and pyridine (1.6 mL, 20 mmol) was dissolved in 100 mL of dichloromethane (DCM) in a round bottom flask that was continuously purged with $N_2$ gas. A solution of 1.36 g (13 mmol) of triphosgene in 10 mL of DCM was added to the reaction mixture with stirring over a two-hour period at room temperature. The reaction progress (molecular weight, Mw and polydispersity index (PDI) were determined using gel permeation chromatography (GPC) using dimethyl formamide (DMF) as the mobile phase, relative to polystyrene standards. Additional 10% (mol) aliquots of triphosgene and pyridine were added until the maximum molecular weight was reached. The addition of 30% (mol) pyridine to the reaction led to cross-linking of the polymer chains and to the formation of the desired cross-linked polymer tissue scaffold. The cross-linked polymer tissue scaffold was successively washed using the following solutions: $H_2O$ (200 mL), isopropyl alcohol (IPA):$H_2O$ (1:1, 200 mL), IPA (200 mL), and hexane (200 mL). The cross-linked polymer tissue scaffold was allowed to dry under $N_2$ gas following vacuum drying at room temperature for 24 hours. The purity and chemical composition of each formulation were confirmed by $^1$H-NMR in $CDCl_3$ (Varian 400 MHz) and is reported below. Chemical shift δ is given in ppm referenced to the internal standard tetramethylsilane (TMS, δ=0 ppm).

Example 1.1. Poly(curcumin-co-50% PEG1k Carbonate) (50CUR50PEG)

$^1$H-NMR ($CDCl_3$, δ, ppm): 7.62 (d, J=8 Hz, 2H, PhCH), 7.16 (br, 6H, Ph), 6.58 (d, J=8 Hz, 2H, PhCHCH), 5.88 (s, 1H, COCH), 4.4 (br, 4H ($CH_2CH_2O)_n$—$CH_2CH_2OCO$), 4.28 (br, 2H, ($CH_2CH_2O)_n$—$CH_2CH_2OH$), 3.9 (s, 6H, Ph-$OCH_3$), 3.7 (br, 2H, ($CH_2CH_2O)_n$—$CH_2CH_2OCO$), 3.5 (br, ($CH_2CH_2O)_n$).

Example 1.2. Poly(curcumin-co-25% PEG1k Carbonate) (75CUR25PEG)

$^1$H-NMR ($CDCl_3$, δ, ppm): 7.63 (d, J=8 Hz, 2H, PhCH), 7.14 (br, 6H, Ph), 6.58 (d, J=8 Hz, 2H, PhCHCH), 5.82 (s, 1H, COCH), 4.4 (br, 4H ($CH_2CH_2O)_n$—$CH_2CH_2OH$), 4.27 (br, 2H, ($CH_2CH_2O)_n$—$CH_2CH_2OH$), 3.9 (s, 6H, Ph-$OCH_3$), 3.7 (br, 2H, ($CH_2CH_2O)_n$—$CH_2CH_2OCO$), 3.5 (br, ($CH_2CH_2O)_n$).

Example 1.3. Poly(curcumin-co-75% PEG1k Carbonate) (25CUR75PEG)

$^1$H-NMR ($CDCl_3$, δ, ppm): 7.62 (d, J=8 Hz, 2H, PhCH), 7.16 (br, 6H, Ph), 6.59 (d, J=8 Hz, 2H, PhCHCH), 5.84 (s, 1H, COCH), 4.42 (t, J=5.05, 4H ($CH_2CH_2O)_n$—$CH_2CH_2OCO$), 4.28 (t, J=5.05, 2H, ($CH_2CH_2O)_n$—$CH_2CH_2OH$), 3.97 (s, 6H, Ph-$OCH_3$), 3.65 (br, 2H, ($CH_2CH_2O)_n$—$CH_2CH_2OCO$), 3.5 (br, ($CH_2CH_2O)_n$).

Example 1.4. Poly(curcumin-co-25% DTE-co-50% PEG1k Carbonate) (25CUR25DTE50PEG)

$^1$H-NMR ($CDCl_3$, δ, ppm): 7.62 (d, J=8 Hz, 2H, PhCH), 7.16 (br, 14H, Ph), 6.59 (d, J=8 Hz, 2H, PhCHCH), 5.84 (s, 1H, COCH), 4.82 (s, 1H, CHN), 4.4 (br, 2H, $CH_3CH_2CO$), 4.3 (br, 4H ($CH_2CH_2O)_n$—$CH_2CH_2OCO$), 4.18 (br, 2H, ($CH_2CH_2O)_n$—$CH_2CH_2OH$), 3.97 (s, 6H, Ph-$OCH_3$), 3.65

(br, 2H, (CH$_2$CH$_2$O)$_n$—CH$_2$CH$_2$OCO), 3.6 (br, (CH$_2$CH$_2$O)$_n$), 3.1 (br, 2H, PhCHCHN), 2.9 (br, 2H, PhCH$_2$CH$_2$), 1.25 (br, 3H, CH$_3$CH$_2$CO).

Example 1.5. Poly(curcumin-co-50% DTE-co-25% PEG1k Carbonate) (25CUR50DTE25PEG)

$^1$H-NMR (CDCl$_3$, δ, ppm): 7.62 (d, J=8 Hz, 2H, PhCH), 7.2 (br, 14H, Ph), 6.59 (d, J=8 Hz, 2H, PhCHCH), 5.85 (s, 1H, COCH), 4.82 (s, 1H, CHN), 4.4 (br, 4H (CH$_2$CH$_2$O)$_n$—CH$_2$CH$_2$OCO), 4.18 (br, 2H, CH$_3$CH$_2$CO), 3.97 (s, 6H, Ph-OCH$_3$), 3.8 (br, 2H, (CH$_2$CH$_2$O)$_n$—CH$_2$CH$_2$OCO), 3.6 (br, (CH$_2$CH$_2$O)$_n$), 3.1 (br, 2H, PhCHCHN), 2.9 (br, 2H, PhCH$_2$CH$_2$), 1.25 (br, 3H, CH$_3$CH$_2$CO).

Example 1.6. Poly(curcumin-co-25% I$_2$DTE-co-50% PEG1k Carbonate) (25CUR25I$_2$DTE50PEG)

$^1$H-NMR (CDCl$_3$, δ, ppm): 7.62 (s, 2H, PhI$_2$CH), 7.62 (d, J=8 Hz, 2H, PhCH), 7.16 (br, 10H, Ph), 6.59 (d, J=8 Hz, 2H, PhCHCH), 5.84 (s, 1H, COCH), 4.82 (s, 1H, CHN), 4.4 (br, 2H, CH$_3$CH$_2$CO), 4.3 (br, 4H (CH$_2$CH$_2$O)$_n$—CH$_2$CH$_2$OCO), 4.18 (br, 2H, (CH$_2$CH$_2$O)$_n$—CH$_2$CH$_2$OH), 3.97 (s, 6H, Ph-OCH$_3$), 3.65 (br, 2H, (CH$_2$CH$_2$O)$_n$—CH$_2$CH$_2$OCO), 3.6 (br, (CH$_2$CH$_2$O)$_n$), 3.1 (br, 2H, PhCHCHN), 2.9 (br, 2H, PhCH$_2$CH$_2$), 1.25 (br, 3H, CH$_3$CH$_2$CO).

Example 1.7. Synthesis of the Model Degradation Product Poly(DTE-co-20% PEG1k Carbonate) (E0020(1k))

E0020(1k) was synthesized as known in the art in order to serve as a control for the in-vitro study.

Example 1B

Similarly anthocyanidin-, catechin-, luteolin-, and quercetin-derived cross-linked polymer tissue scaffolds are prepared as for the curcumin-derived cross-linked polymer tissue scaffolds, following the procedure of Example 1A.

Example 2. Thermal Analysis

The glass transition temperatures (Tg) of the cross-linked polymer tissue scaffolds were determined in the second heat cycle as the midpoint of the transition using differential scanning calorimetry (DSC) (DSC2920, TA Instruments, New Castle, Del.) with a heating rate of 10° C. min$^{-1}$.

Example 3. Mechanical Testing

Elastic moduli (E) of the cross-linked polymer tissue scaffolds were measured by compression of wet samples that were swelled for 24 h prior to testing (three samples per composition) using a Bose Electroforce® (Bose, Eden Prairie, Minn.) tester equipped with a 10 Newton (N) load cell at 25° C. The compressive elastic modulus was obtained by the initial (straight line) linear slope of the stress vs. strain curve.

Example 4. Swelling Studies

The swelling study was conducted by immersing 20 mg cross-linked polymer tissue scaffolds (n=3) into 1 mL of de-ionized water at 25° C. At various time intervals, the excess water on the swollen surface was wiped with a filter paper and the weight of the swollen sample was determined. Analysis of swelling was undertaken as known in the art using Eq. 1. The swelling percentages (SP) were fitted to a Fickian model, where $W_t$ is the swollen mass at time t, $W_0$ is the mass of dry samples and $K_s$ is the swelling rate.

$$SP\ (\%) = [(W_t - W_0)/W_0]100 = K_s t^{0.5} \qquad \text{Eq. 1}$$

Example 5. Mass Loss

The mass loss (ML) study was conducted by immersing 20 mg of cross-linked polymer tissue scaffold (n=3) into 1 mL of PBS (pH=7.4) and incubating at 37° C. At various time intervals, the composition was washed with de-ionized water, freeze-dried, and weighed. The mass loss was determined using Eq. 2 where $M_t$ is the mass at time t, and $M_0$ is the initial sample mass.

$$ML\ (\%) = [(M_0 - M_t)/M_0]100 \qquad \text{Eq. 2}$$

Example 6. Pore Size Evaluation

The pore size was measured following standard procedures using DSC. In this measurement, the enthalpic change of the cross-linked polymer tissue scaffold placed in the chamber was observed, while decreasing the temperature from 0 to −30° C. at a rate of 1° C. min$^{-1}$. The numerical expression of the variation of pore radius (Rp) with water triple point temperature is given in Eq. 3 where $\Delta T = T - T_{tri}$ is the shift in the triple point temperature.

$$R_p (nm) = -64.67/\Delta T + 0.57 \qquad \text{Eq. 3}$$

Example 7. In Vitro Curcumin Release from Matrices

An in vitro curcumin release study was conducted by immersing each cross-linked polymer tissue scaffolds (1 mg) into release buffer. The volume of the release buffer (1-3 mL) was adjusted to maintain a constant sink condition depending on the incubation duration. The composition of the release buffer was optimized to ensure that the curcumin released from the cross-linked polymer tissue scaffold was soluble and stable in the buffer. The release buffer consisted of PBS (pH=7.4) containing 10% (w/v) Tween 80, 0.1% (w/v) N-acetylcysteine, and 0.01% (w/v) butylated hydroxytoluene (BHT). The samples (n=3) were incubated over 50 days at 37° C. At predetermined time-points, the entire release buffer was removed and replaced with fresh buffer. The withdrawn release buffer was frozen, dried and saved at −18° C. until it was analyzed.

Curcumin concentration in the release buffer was quantified by fluorescence. 2 mL of DMSO was added to the dried release buffer sample and shaken for 1 h to extract the curcumin. 200 μL of the extracted curcumin in DMSO, placed in 96-well, black, clear bottom plates, was measured using a fluorescence plate reader (Tecan, Männedorf, Switzerland) by applying wave length excitation of 450 nm and emission of 535 nm. The calibration standard was prepared by adding to a freeze-dried release buffer (2 mL), curcumin that was dissolved in DMSO (2 mL) in concentrations of 2000, 1000, 500, 250, 125, 62.5, 31.25, 15.6, 7.8, 3.9 ng/mL.

Example 8. In Vitro Cytotoxicity Studies

MDA-MB-231 breast cancer cells and primary human dermal fibroblasts (HDFs) were obtained from the ATCC (USA). Both cell types were cultured in DMEM supplemented with 10% fetal bovine serum (FBS) and 25 µg/mL Gentamicin. For toxicity studies HDFs were seeded at 5,000 cells per well/1 mL medium in a 12-well plate and allowed to reach confluency prior to application of experimental conditions. MDA-MB-231 cell were seeded in 12-well plates at a seeding density of 5,000 per well/1 mL medium and incubated at 37° C. in a humidified atmosphere of 95% air and 5% $CO_2$ for 24 h prior to application of experimental conditions. Experimental conditions included: (a) cross-linked polymer tissue scaffolds containing curcumin concentrations of 50 to 45,000 µM placed into the transwell inserts (Costar, membrane pore size: 3.0 mm, Pittsburgh, Pa.); (b) 2 to 50 µM curcumin dissolved in the growth medium (using 1% DMSO); (c) the possible degradation products PEG1k (3 mM) and E0020(1k) (37 mg non-dissolved); and (d) a positive control of culture media alone (e) a negative control of 10% DMSO.

Cells subjected to these experimental conditions were allowed to culture for 6 days at which point cell viability was measured using Alamar blue metabolic assay. The reagent solution (10%) was added to each well and incubated for 2 h at 37° C. The supernatant from each well was transferred to a 96-well plate and was measured using a fluorescence plate reader (Tecan, Männedorf, Switzerland) by applying wavelength excitation of 560 nm and read it at emission of 590 nm, which is directly correlated to the viable cell number, and inversely correlated with the toxicity of the cross-linked polymer tissue scaffolds. The mean absorbance for each treatment was determined and then expressed as a percent of viability relative to the control. All conditions were conducted with at least three replicate wells within an individual experiment and an overall n>3 for individual experiments.

Example 9. Lentiviral Fluorescent Labeling of Cells

The cytotoxic selectivity of curcumin-derived cross-linked polymer tissue scaffold toward MDA-MB-231 cells was further assessed in a dynamic co-culture system as described below and in Example 10:

HDF and MDA-MB-231 cells were fluorescently labeled with lentiviruses expressing a peptide, coined Lifeact, which binds to polymerized actin that had been fused with turboGFP and mRFP. For the Lifeact turboGFP (LAG), a forward primer containing an AsiSI enzyme site, the Lifeact sequence, and the 5' region of turbo GFP omitting the start codon was synthesized (5'-CATACGCGATCGCAC-CATGGGTGTGGCCGATCTGATTAAGAAGTTCGAAT-CAATTAG TAAGGAAGAGGGTGGATCAGGT-GAGAGCGACGAGAGCGGCCTGCCCG 3' (SEQ ID NO. 1)), and paired with the reverse primer (5' CATACTGCG-CAAATAAGAAGTGGCCGTAGACGTAG 3' SEQ ID NO. 2) containing an MluI enzyme site and the 3' terminal end of turboGFP. PCR (polymerase chain reaction) was conducted using turboGFP as the template yielding a 775 base pair product that was digested by AsiSI and MluI and cloned into the pLKO.1 lentiviral vector (Addgene, Cambridge, Mass.). This was similarly performed to create the Lifeact mRFP (LAR) genetic sequence within the pLKO.1 lentiviral vector (forward primer (5'-CATACGCGATCGCACCAT GGGT-GTGGCCGATCTGATTAAGAAGTTCGAATCAATTAG-TAAGGAAGAGGGTGGAT CAGGTGCCTCCTCCGAG-GACGTCATCAAGG-3' (SEQ ID NO. 3)), reverse primer (5'-TGCGCAAATCCGC GGCCACCTCACCGC 3' (SEQ ID NO. 4)).

Integrated DNA Technologies in Coralville, Iowa, synthesized all primers and GENEWIZ in South Plainfield, N.J. conducted sequencing to confirm insertion and sequence accuracy. Lentivirus of LAR and LAG was synthesized using established procedures. Briefly, LAR or LAG pLKO.1 plasmid was co-transfected at a ratio of 3 µg: 1.5 µg: 2 µg with pMD2.G and Pax2 plasmids (Addgene, Cambridge, Mass.) respectively via FuGENE 6 (Roche, Indianapolis, Ind.) into 80% confluent HEK293FT cells in serum free media. Media was changed after 24 hours to contain serum and supernatant-containing virus, and was harvested at 48 and 72 hours post-transfection. Virus containing medium was passed through 0.45 µm nylon filters (Fisher 09-719D, Pittsburgh, Pa.) and either used directly to infect cells or frozen at −80° C. for future use. HDF and MDA-MB-231 were subjected to two successive 24 hour infection cycles and non-infected cells were removed through treatment of G418 (Sigma, USA) since the pLKO.1 vector expresses a resistance gene to this drug.

Example 10. Co-Culture Experiments

LAR-expressing HDF cells were grown to confluency in 12 well plates and LAG-S expressing MDA-MB-231 cells were plated at an initial density of 5000 per well on top of the confluent layer of HDFs. LAG-expressing MDA-MB-231 cells were allowed to adhere overnight and the following day the experimental conditions were applied; 50CUR50PEG containing curcumin concentrations of 50 to 62,000 µM was placed into the top of the transwell containing the cell co-cultures. Cells were analyzed after 6 days and the abundance of LAG-expressing MDA-MB-231 cells was assessed by fluorescent microscopy.

Example 11. Statistics Analysis

Assignments to treatments were made at random. Statistical differences were determined using a 2-way ANOVA followed by Tukey's post hoc test for comparison of treatments. All statistical analyses were performed using SPSS18 statistical software (USA). All data are presented as a mean value with its standard error indicated (mean±SE). p-values of less than 0.01 were considered significant.

Example 12. Loading of Drugs Into Cross-Linked Polymer Tissue Scaffolds

Tamoxifen is loaded into the cross-linked polymer tissue scaffolds of Example 1A, for example, Poly(curcumin-co-25%$I_2$DTE-co-50% PEG1k carbonate) of Example 1.6 (25CUR25$I_2$DTE50PEG), using a swelling method, which comprises treating the polymer with a solution of tamoxifen in dichloromethane, evaporation of the solvent, washing with methanol to remove surface (unbound) tamoxifen, and hydration of the tamoxifen-loaded polymer to form the cross-linked polymer tissue scaffolds. This method provides excellent loading efficiency (87-91%), with high loadings (5-40 weight %) of incorporated tamoxifen.

Analogously, Tamoxifen can be loaded into the cross-linked polymer tissue scaffolds of Example 1B.

Similarly, cisplatin or paclitaxel can be loaded into the cross-linked polymer tissue scaffolds of Examples 1A or 1B.

Example 13. Comparison of Inventive Cross-Linked Polymer Tissue Scaffolds

In one embodiment of the invention, various curcumin-derived cross-linked polymer tissue scaffolds (FIG. 1), containing various concentrations of curcumin were synthesized by condensation polymerization of curcumin, PEG1k and, optionally DTE (desaminotyrosyl-tyrosine ethyl ester), in the presence of triphosgene and the catalyst pyridine as described above. To simplify the naming of the curcumin-derived cross-linked polymer tissue scaffolds, the notation CURXDTEYPEGZ is used to name poly(X %-curcumin-co-Y %-DTE-co-Z %-PEG carbonate)s.

Growth of the polymer chains to a relatively high weight-average molecular weight (70-200 kDa) while preventing the inter-chain cross-linking, can be achieved by using an initial exact stoichiometry between pyridine and monomers (2:1, respectively). Pyridine preferentially catalyzed the reaction of the more acidic phenolic groups of the curcumin molecule rather than its enolic carbonyl group; hence it leads to the formation of a linear polymer. After reaching the maximum molecular weight achievable by adding triphosgene, addition of excess pyridine (3:1, pyridine: monomer or greater) enabled the enolic hydroxyl to react and to cross-link the polymer chains to form the desired cross-linked polymer tissue scaffold. Table 2 summarizes the maximum molecular weight (Mw) and the polydispersity (PDI) values of the polymers before cross-linking. Increasing the concentration of PEG1k from 25% to 50% led to a significant increase in the maximum molecular weight that can be reached before cross-linking. Even when DTE was added to the composition, the maximum molecular weight was dependent on PEG content.

Determination of curcumin content in synthesized cross-linked polymer tissue scaffolds was performed by integration of the $H^1$-NMR peaks of COCH (5.84 ppm) present in curcumin, $(CH_2CH_2O)_n$—$CH_2CH_2OCO$ (4.41 ppm) of PEG1k and CHN (4.82 ppm) of DTE (Table 2). The experimental molar ratio of curcumin content within the cross-linked polymer tissue scaffolds was found to be close to theoretical content with 4 to 20% deviation. Higher deviations from calculated curcumin content occurred in high PEG content cross-linked polymer tissue scaffolds. Noteworthy is the relatively high curcumin content (up to 75 mol %) in the cross-linked polymer tissue scaffolds.

Thermal analysis (Table 2) indicated that the cross-linked polymer tissue scaffolds, except 25CUR75PEG, are amorphous, as evident from the presence of a glass transition (Tg) and the absence of a clear melting temperature (Tm). The crystalline structure of 25CUR75PEG (Tm=36.3) can be attributed to the high content of crystalline PEG1k chains. Moreover, the increases in Tg were correlated to the increasing amount of the rigid monomers (curcumin and DTE) and the decreases of flexible PEG1k content: −25° C. for 25CUR25DTE50PEG to as high as −11° C. for 25CUR50DTE25PEG. It was noted that 25CUR75PEG completely dissolved in water within 10 minutes, thus making this material less suitable for use as a long-term drug delivery matrix or tissue filler.

Figure 2:
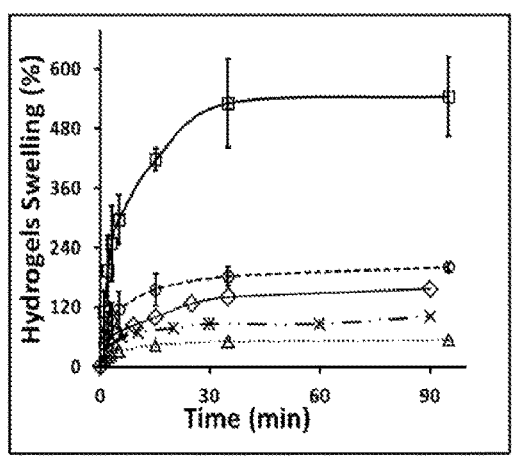
FIG. 2 shows the swelling percentage curves over the initial 95 min of 75CUR25PEG (Δ) 50CUR50PEG (○), 25CUR50DTE25PEG (X) 25CUR25DTE50PEG (□) and 25CUR25I$_2$DTE50PEG (◇) cross-linked polymer tissue scaffold.

The swelling ability of 25CUR50DTE25PEG, 25CUR25DTE50PEG, 50CUR50PEG and 75CUR25PEG was studied using an immersing technique, and evaluated using Tasdelen's method. As shown in FIG. 2, all samples reached a plateau in approximately 40 min, regardless of composition. However, an increase in the cross-link density from 25 to 75% (curcumin content) caused a significant decrease in the swelling ability of these cross-linked polymer tissue scaffolds: maximum swelling of 550, 190 and 50% for 25CUR25DTE50PEG, 50CUR50PEG and 75CUR25PEG, respectively. Further, comparing the swelling abilities of 25CUR50DTE25PEG and 25CUR25DTE50PEG (6 fold) emphasized the dominating role of hydrophilic PEG1k in the ability of the cross-linked polymer tissue scaffolds to swell. Swelling profiles were modeled with standard Fickian diffusion models by plotting swelling percent against time to the half-power (Eq. 1):

$$SP\ (\%)=[(W_t-W_0)/W_0]100=K_s t^{0.5} \qquad \text{Eq. 1}$$

A straight line was obtained for the first 30% of swelling time (25 min), which represents the swelling rate ($K_s$) for each cross-linked polymer tissue scaffold. The model fit resulted in all $R^2$ values being above 0.95. The calculated $K_s$ values reflected an increase in the swelling ability of 75CUR25PEG, 25CUR50DTE25PEG, 50CUR50PEG and 25CUR25DTE50PEG by rising from 0.12, 0.31, and 0.46 up to 1.34 $s^{-1}$, respectively.

The elastic moduli found by the compression of the wet cross-linked polymer tissue scaffolds to 50% height are summarized in Table 2. As expected, an increase in the elastic modulus was measured with increasing the cross-link concentration in the tested cross-linked polymer tissue scaffolds. The mechanical stiffness of 50CUR50PEG, with a higher cross-linking degree than 25CUR25DTE50PEG, was three times stronger. However, 25CUR50DTE25PEG which contains the same degree of cross-linking as 25CUR25DTE50PEG, but half of the PEG1k content, showed an approximate 7-fold increase in elastic modulus. These results are in agreement with the swelling study and the thermal analysis, thus confirming the interplay between the cross-linking degree, the PEG1k content, and physical properties of the final cross-linked polymer tissue scaffold.

Increasing the content of the hydrophobic curcumin while decreasing the content of the hydrophilic PEG1k led to the formation of a cross-linked polymer tissue scaffold with higher hydrophobic cross-linking density that was not capable of absorbing as much water, thereby displaying a higher stiffness. This trend was clearly observed with 75CUR25PEG, which possessed the highest amount of cross-linking and the lowest amount of PEG1k, and was found to be the stiffest cross-linked polymer tissue scaffold with the lowest swelling ability. The elastic moduli of all tested cross-linked polymer tissue scaffolds were in the range of the modulus of elasticity of most biological tissues that are soft viscoelastic materials (0.1 kPa-100 kPa). Specifically, the elastic moduli of 50CUR50PEG and 25CUR50DTE25PEG were similar to breast tissue, where the majority of breast is normal glandular and fat tissue that exhibits elastic moduli of 33 and 25 kPa, respectively.

Figure 3:
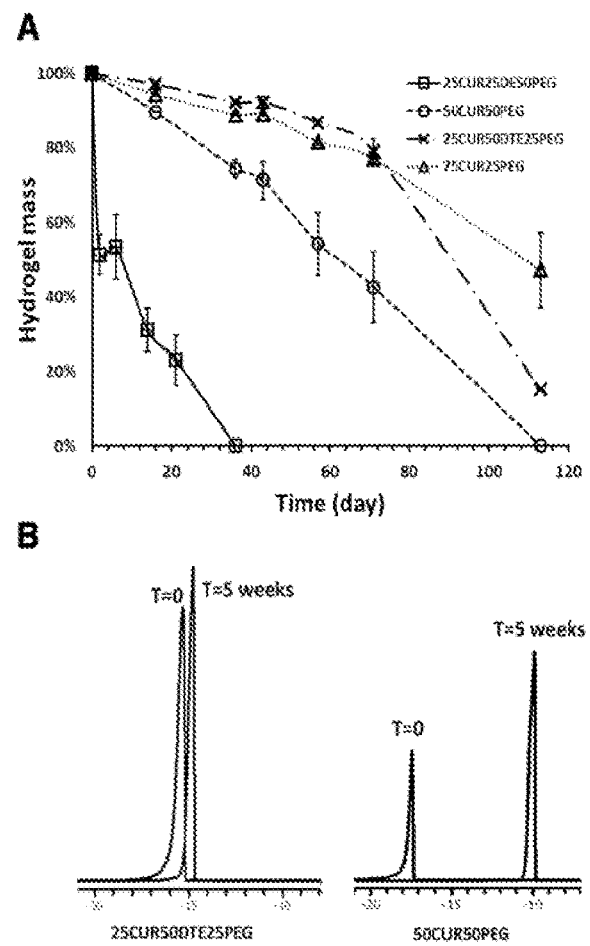
FIG. 3 displays (A) Curcumin-derived cross-linked polymer tissue scaffold mass as a function of time; and (B)

Mass loss of 75CUR25PEG, 50CUR50PEG, 25CUR50DTE25PEG and 25CUR25DTE50PEG during incubation in PBS solution at 37° C. is presented in FIG. 3A. Mass loss trends were found to be similar to those observed for swelling. Cross-linked polymer tissue scaffolds containing a low PEG1k amount and a high cross-link degree lost mass much more slowly than those with a greater content of PEG1k and a lower degree of cross-linking. The materials with a high PEG1k concentration absorbed much more water and thus have increased hydrolysis (and hence mass loss) rates. $^1$H-NMR analysis of the incubation media in the mass loss study at 5 and 20 days indicated that the degradation products contained eight times as much PEG1k as curcumin. This result emphasized that the first degradation product to be dissolved and washed out of the cross-linked polymer tissue scaffold was water soluble PEG1k, while the degradation products such as curcumin and DTE, which are not soluble in PBS, remained within the matrix.

Evaluation of the degradation kinetics by GPC was not possible due to the insolubility of the cross-linked polymer tissue scaffold in all solvents commonly used for GPC.

Hence, tracking the changes in the pore size of the cross-linked polymer tissue scaffolds by measuring the freezing point of water (Eq. 3) was used to confirm the degradation of the matrix.

$$R_p(\text{nm}) = -64.67/\Delta T + 0.57 \qquad \text{Eq. 3}$$

50CUR50PEG and 25CUR50DTE25PEG were chosen for this study since they represent very different compositions. FIG. 3B shows that the water freezing point of 50CUR50PEG was lower than that for 25CUR50DTE25PEG, suggesting that 50CUR50PEG has smaller pore size. This was expected due to the stiffer and most likely poorly packed polymer chains in 25CUR50DTE25PEG. Incubation of 25CUR50DTE25PEG for 5 weeks led to a limited change in the water freezing point, while 50CUR50PEG showed a significant increase in the freezing point with the increase in the average pore diameter from 4.3 to 7.1 nm. These results validated that 50CUR50PEG underwent faster degradation causing loss of cross-linking over time, which led to large pores in the cross-linked polymer tissue scaffold.

Based on the results, three compositions (25CUR25DTE50PEG, 50CUR50PEG and 75CUR25PEG) that showed significant differences in swelling, mechanical, and mass loss were evaluated for curcumin release. The release of curcumin is reportedly controlled by overall hydrophilicity of the matrix that is correlated to its swelling ability, followed by chemical hydrolysis of the carbonate bond and diffusion of the curcumin into the solution. The initial hydrolysis of the carbonate linkage produced some of the free curcumin and a variety of curcumin conjugates (curcumin linked to PEG and/or DTE monomers/oligomers). These conjugates further hydrolyzed to release free curcumin, with the rate of hydrolysis likely dependent on the conjugate composition. To determine the concentration of released curcumin present as either free curcumin or curcumin conjugates, samples were examined using fluorescence analysis.

FIG. 4 depicts the cumulative curcumin release profiles for 25CUR25DTE50PEG, 50CUR50PEG and 75CUR25PEG observed over 50 days. In all samples, a small burst release was observed in the first 24 hours, followed by a relatively constant release over the remainder of the study. Further analysis of these results revealed that the release kinetics were dependent on both the water uptake and curcumin concentration of the cross-linked polymer tissue scaffolds, where the highest and lowest content curcumin samples (75CUR25PEG and 25CUR25DTE50PEG) released similar amounts of curcumin over the course of the study. In the first three weeks the release kinetics in both samples were governed by the swelling ability/water uptake of each sample. Relatively high water uptake (550% after 1 hour) of 25CUR25DTE50PEG led to fast degradation and subsequent curcumin release. On the other hand, the high hydrophobic content of 75CUR25PEG most likely slows down the water uptake, resulting in slower curcumin release.

After 3.5 weeks of the study, the release kinetics were dependent on the remaining curcumin content in each sample: in fast releasing 25CUR25DTE50PEG the amount of curcumin was low compared to a high content in slow releasing 75CUR25PEG. Further, after 36 days the 25CUR25DTE50PEG matrix started to fall apart and curcumin release was inconsistent among tested replicates. It thus appears that 50CUR50PEG possesses a balance between the two parameters, curcumin concentration and swelling ability, which led to stable curcumin release. The slow release profile of the curcumin-derived cross-linked polymer tissue scaffolds, which is degradation controlled, can be compared to encapsulated curcumin release from a self-assembling peptide hydrogel. At the same fixed curcumin concentration the daily release of the encapsulated curcumin was observed to be 2.8-4.5 µM, while in the curcumin-derived cross-linked polymer tissue scaffold system, the daily curcumin release was significantly lower, at 0.2-0.5 µM.

The potential of 25CUR25DTE50PEG, 50CUR50PEG and 75CUR25PEG as chemo-therapeutic agents was evaluated in vitro using MDA-MB-231 breast cancer cells. Cell viability was assessed by placing the cross-linked polymer tissue scaffolds within the upper chamber of a transwell so that any effect on cells was due to compounds released from the cross-linked polymer tissue scaffolds during hydrolysis and not due to mechanical disruption. Measuring cell viability after 6 days revealed that the effects on the MDA-MB-231 breast cancer cells varied depending on the composition of the curcumin cross-linked polymer tissue scaffolds (FIG. 5A) where 25CUR25DTE50PEG that released a relatively high concentration of curcumin conjugates exhibited the highest cytotoxicity. However, as opposed to the previous data of curcumin release (FIG. 4), the cytotoxicity of 50CUR50PEG, which released the smallest amount of curcumin conjugates, showed significantly higher cytotoxicity versus the fast curcumin release 75CUR25PEG.

These cytotoxicity results can be attributed to the random degradation of the cross-linked polymer tissue scaffolds, which caused the release of different amounts of water-soluble conjugates, most likely curcumin-PEG conjugates. Increasing PEG content led to release of greater amounts of water-soluble and cell-available curcumin conjugates. These were gradually hydrolyzed by the cancer cells' lysosomes, and released active, free curcumin. To better visualize this data, the cytotoxicity was re-plotted (FIG. 5B) for each of the cross-linked polymer tissue scaffolds using values of released curcumin extrapolated from the release profile of each cross-linked polymer tissue scaffold as reported in FIG. 4. Cytotoxicity of cross-linked polymer tissue scaffolds was compared against free curcumin dissolved at 4 mg/mL in DMSO and diluted into cell culture media with a maximum final DMSO concentration of 1% v/v.

The $IC_{50R}$ values for the cross-linked polymer tissue scaffolds on MDA-MB-231 cells were found to be 14, 14, 9 and 39 µM/mL for free curcumin, 25CUR25DTE50PEG, 50CUR50PEG and 75CUR25PEG, respectively. These results indicated that the potency of the curcumin released from the cross-linked polymer tissue scaffolds fell within a similar range as free curcumin, with differences intrinsic to each formulation, while 50CUR50PEG obtained even higher cytotoxicity against MDA-MB-231 cells. However, addition of free curcumin to the media resulted in curcumin uptake by cells or degradation in less than 48 hours, while the cross-linked polymer tissue scaffolds continued to release active curcumin until they were full degraded.

To further evaluate the potential of 50CUR50PEG cross-linked polymer tissue scaffold as an implantable device, its toxicity was evaluated on quiescent non-cancerous cells using confluent layers of HDFs. 50CUR50PEG showed no measurable cytotoxicity even at high concentrations of the cross-linked polymer tissue scaffold and released curcumin concentration (FIG. 6). The cytotoxic selectivity of 50CUR50PEG toward MDA-MB-231 cells was further assessed in a dynamic co-culture system. Lentiviruses were employed to insert genetic sequences into HDFs and MDA-MB-231 cells that induce expression of green fluorescent protein (GFP) and red fluorescent protein (RFP), respectively, on the two cell types. RFP-expressing HDFs (RFP-HDF) were grown to confluency and GFP-expressing MDA-MB-231 (GFP-MDA-MB-231) cells were seeded on top of this monolayer. GFP-MDA-MB-231 cells not only became attached to the RFP-HDF monolayer but a significant number of cells appeared to intercalate into the monolayer of RFP-HDFs. Treatment of these co-cultures with the 50CUR50PEG resulted in selective depletion of GFP-MDA-MB-231 cells. These results reinforce the earlier findings of selective toxicity of released curcumin toward cancer cells through the lack of toxicity to non-cancerous quiescent HDFs.

Example 14. Preparation of Poly(60% $I_2$DTE-co-20% $I_2$DT-co-20% PEG2K Carbonate)

Into a three necked round-bottomed flask, equipped with a mechanical stirrer, a thermometer, a reflux condenser and a rubber septum were added 18.3 g (0.03 mol) of $I_2$DTE, 6.38 g (0.01 mol) of $I_2$DTtBu, 20 g (0.01 mol) of PEG2000, and 300 ml of methylene chloride. On stirring a clear light yellow solution was obtained. To this was added 15.1 ml (0.15 mol) of pyridine. In a gas tight plastic syringe was placed 30 ml of a 20% solution of phosgene in toluene (0.0576 mol), which was added to the reaction flask over 3 h using a syringe pump. The molecular weight was determined by analyzing an aliquot of the reaction mixture by GPC. Additional phosgene solution (up to 10%) was needed to achieve desired molecular weight. The reaction mixture was quenched with 110 ml of THF and 10 ml of water. The polymer was precipitated by adding the reaction mixture to 1.5 L of cold 2-propanol in high speed Waring blender.

The resulting gluey polymer was ground with two portions of 0.5 L 2-propanol. The fine granular polymer particles were isolated by filtration and dried in a vacuum oven. To remove the t-Butyl protecting group, the polymer was dissolved in trifluoroacetic acid to obtain a 20% solution. After stirring the solution at room temperature for 4 h, the polymer was precipitated by adding to 2-propanol and then further grinding with 2-propanol to remove the excess TFA. The product was isolated by filtration, washed with IPA and dried in vacuum oven.

Those skilled in the art will recognize that radio-opaque bromine-substituted polymers can be similarly prepared by replacing iodine with bromine in the starting materials.

Example 15. Preparation of Poly(I2DTE-co-2.5 mole % PEG2K Carbonate)

A polymer containing 97.5% mole percent $I_2$DTE and 2.5% poly(ethylene glycol) of molecular weight 2000 (poly (97.5%$I_2$DTE-co-2.5% PEG2K carbonate)) was prepared as follows. Into a three necked round-bottomed flask, equipped with a mechanical stirrer, a thermometer, a reflux condenser and a rubber septum, were added 29.7 g (0.0488 mol) of $I_2$DTE, 2.5 g (0.00125 mol) of PEG2000, and 215 ml of methylene chloride. On stirring a clear light yellow solution was obtained. To this was added 15.1 ml (0.15 mol) of pyridine. In a gas tight plastic syringe was placed 30 ml of a 20% solution of phosgene in toluene (0.0576 mol), which was added to the reaction flask over 3 h using a syringe pump. The molecular weight was determined by analyzing an aliquot of the reaction mixture by GPC. Additional phosgene solution (up to 10%) was added to achieve the desired molecular weight. The reaction mixture was quenched with 110 ml of tetrahydrofuran and 10 ml of water. The polymer was precipitated by adding the reaction mixture to 1.5 L of cold 2-propanol in high speed Waring blender. The resulting polymer was ground with two portions of 0.5 L 2-propanol. The fine granular polymer particles were isolated by filtration and dried in a vacuum oven.

Example 16. Formation of Microbeads

A 5% w/w DMSO solution of the polymer of Example 2 was prepared by dissolving 0.650 g polymer in 12.35 g DMSO. A precipitation solution was prepared by adding 3 ml of a 10 vol % aqueous solution (from concentrate) of ALCONOX surfactant to 300 ml water. The precipitation solution was placed in a 600 ml container and stirred on a slow setting (<100 RPM). Adding the DMSO polymer solution to the precipitation solution in a drop-wise fashion from a syringe through a 26-gauge needle allows for polymer spheres to precipitate. The 26-gauge needle was ground to a point to buff off the silicone coating. This reduces surface tension, resulting in smaller drops of polymer when dispensed.

The precipitated polymer spheres were isolated through a filtered drop funnel and allowed to air dry. The spheres were then cryogenically ground in a coffee grinder at about 20,000 RPM with added $CO_2$. The ground particles were then dried overnight in a vacuum oven at 50° C. under dynamic vacuum. The dried spheres were then manually sieved into the following particle ranges:
90-180 micron diameter
180-300 micron diameter
300-500 micron diameter
500-710 micron diameter.

Example 17. Preparation of Poly($I_2$DTE-co-2.5 mole % PEG$_{2k}$ Adipate)

The diphenol $I_2$DTE (2.97 g, 4.87 mmol), PEG2000 (0.250 g, 0.125 mmol) and adipic acid (0.731 g, 5.04 mmol) and 0.4 g of DPTS (dimethylamonopyridyl-paratoluene sulfonate, catalyst) were weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Example 18. Polymerization of Poly(60% $I_2$DTE-co-20% $I_2$DT-co-20% PEG$_{2k}$ Adipate)

The diolic components (1.83 g, 3.00 mmol of $I_2$DTE, 0.638 g, 1.00 mmol $I_2$DTtB, and 2.000 g 1.00 mmol of PEG2000), and the diacid (0.731 g, 5 mmol adipic acid) and 0.4 g, of DPTS were weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture, with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Deprotection:

The resulting polymer is dissolved in trifluoroacetic acid (10% w/v) and allowed to stir overnight. The following day, the polymer is precipitated in isopropanol using a blender for mixing. The polymer is then ground twice with fresh isopropanol, filtering with a fritted filter between washes. Then the polymer is dried under nitrogen, followed by drying in a vacuum oven.

Example 19. Preparation of Poly($I_2$DTE-co-2.5 Mole % $PEG_{2k}$ Sebacate)

The diphenol $I_2$DTE (2.98 g, 4.89 mmol), PEG2000 (0.250 g, 0.125 mmol) and sebacic acid (1.01 g, 5.00 mmol) and 0.4 g of DPTS are weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture, with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Example 20. Preparation of Tri-Iodinated-DTE ($I_2$DITE)

Tri-iodinated monomer ($I_2$DITE) was prepared using procedures similar to those published in the literature by substituting $I_2$DAT in the place of DAT and ITE in the place of TE. In a typical procedure 85.8 g (0.255 mol) of 3-iodotyrosine ethyl ester (ITE), 104 g (0.250 mol) of $I_2$DAT and 3 g (0.025 mol) 1-hydroxybenzotriazole were stirred with 500 ml of tetrahydrofuran in a 1 liter round-bottomed flask. The flask was cooled in an ice-water bath to 10-18° C. and 50 g (0.255 mol) of EDCI was added and stirred for 1 h at 15-22° C. This was followed by stirring of the reaction mixture at ambient temperature for 5 h. The reaction mixture was concentrated to 250 ml and then stirred with 1 L of water and 1 L of ethyl acetate. The lower aqueous layer was separated and discarded using a separatory funnel. The organic layer was sequentially washed with 500 ml each of 0.4 M HCl, 5% sodium bicarbonate solution and 20% sodium chloride solution. After drying over anhydrous sodium sulfate, the organic layer was concentrated to syrup and triturated by stirring with hexane. An off white solid is obtained. The product is characterized by HPLC and $^1$H NMR.

Example 21. Preparation of Tetraiodinated DTE ($I_2DI_2$TE)

DTE (16.4 g, 0.046 mol) was dissolved in 300 ml of 95% ethanol. To the solution with stirring was added 46 g (0.19 mol) of PyICl. The solution was stirred for 2 h when the solid slowly dissolved to give a light yellow solution. This was added over 30 min, with stirring, to 1 liter of water containing 10 g sodium thiosulfate. An off-white solid separated and was isolated by filtration and washed with several portions of deionized water.

The wet cake (ca 150 g) was heated with 1.5 L of ethanol until it dissolved and then allowed to cool to room temperature. The white crystalline solid formed was isolated by filtration and washed with 95% ethanol and dried. 32 g (81%) of the dry product was obtained. The product was characterized by HPLC and $^1$H NMR.

Example 22. Tri-Iodinated Polymer Containing Poly(Ethylene Glycol)

A polymer containing 80% mole percent $I_2$DITE and 20% poly(ethylene glycol) of molecular weight 2000 (poly(80% $I_2$DITE-co-20% PEG2K carbonate)) was prepared as follows. Into a three necked round-bottomed flask, equipped with a mechanical stirrer, a thermometer, a reflux condenser and a rubber septum were added 6.0 g (8.1 mmol) of $I_2$DITE and 4.1 g (2.05 mmol) of PEG2000, and 66 ml of methylene chloride and 3.1 ml (39 mmol) of pyridine. On stirring a clear almost colorless solution was obtained. In a gas tight plastic syringe was placed 6.5 ml of a 20% solution of phosgene in toluene (12.5 mmol), which was then added to the reaction flask over 3 h using a syringe pump. The molecular weight was determined by analyzing an aliquot of the reaction mixture by GPC. A polystyrene equivalent Mw of 200,000 was obtained. The reaction mixture was quenched with 55 ml of tetrahydrofuran and 5 ml of water. The polymer was precipitated by adding the reaction mixture to 1 L cold 2-propanol in a high speed Waring blender. The resulting gluey polymer was ground with two portions of 0.5 L 2-propanol. The fine granular polymer particles were isolated by filtration and dried in a vacuum oven.

Example 23. Tetra-Iodinated Polymer Containing Poly(Ethylene Glycol)

A polymer containing 80% mole percent $I_2DI_2$TE and 20% poly(ethylene glycol) of molecular weight 2000 (poly (80% $I_2DI_2$TE-co-20% PEG2K carbonate)) was prepared as follows. Into a three necked round-bottomed flask, equipped with a mechanical stirrer, a thermometer, a reflux condenser and a rubber septum were added 1.55 g (1.80 mmol) of $I_2DI_2$TE and 0.9 g (0.45 mmol) of PEG2000, and 20 ml of methylene chloride and 0.68 ml (8.6 mmol) of pyridine. On stirring a clear almost colorless solution was obtained. In a gas tight plastic syringe was placed 1.4 ml of a 20% solution of phosgene in toluene (2.7 mmol), which was then added to the reaction flask over 3 h using a syringe pump. The molecular weight was determined by analyzing an aliquot of the reaction mixture by GPC. A poly-styrene equivalent Mw of 25,000 was obtained. The reaction mixture was quenched with 18 ml of tetrahydrofuran and 2 ml of water. The polymer was precipitated by adding the reaction mixture to 200 ml of cold 2-propanol in a beaker using a magnetic stirrer. The resulting gluey polymer was ground with 200 ml of 2-propanol. The polymer obtained was still gluey probably due to the low molecular weight and high poly(ethylene glycol) content.

Example 24. Preparation of Polymer and Nanosphere-Solute Formulations

Polymer Preparation and Characterization:

The triblock copolymer was synthesized in a one-pot reaction at 20° C. using in situ carbodiimide coupling of the PEG and oligo (DTO-SA) as described in U.S. Pat. No. 8,591,951, the contents of which are incorporated herein by reference, as disclosed below. The chemical structure and purity of the copolymer was confirmed by $^1$H NMR (d6-DMSO, Varian Unity 300 spectrophotometer, Palo Alto, Calif.). Molecular weights (Mn and Mw) were determined using gel permeation chromatography, GPC (PL-gel columns, pore size 105 and 104 Å, Perkin-Elmer, Shelton, Conn.; Waters 410 RI detector) with 1 mL/min THF flow rate and polystyrene standards as Mw markers.

Preparation of Nanosphere-Solute Formulations:

Nanosphere complexes with or without solute compounds were prepared by combining 60 mg of triblock copolymer with 600 μg of either DAF or curcumin or Nile Red in 600 μL of DMF. These solutions were added drop-wise to 14.4 mL of deionized water with constant stirring. In order to remove particles greater than 220 nm in diameter, the resulting turbid aqueous dispersions were filtered through 0.22 μm PVDF syringe filters (Millipore, Bedford, Mass.), and the filtrate was used for all subsequent characterizations.

We refer to purified nanospheres as those that were processed as follows: the self-assembled nanosphere-solute suspensions were filtered through 0.22 μm filters; the filtered suspensions were isolated by ultracentrifugation of 12.25 mL nanosphere solutions at 65 000 rpm (290 000×g) for 3 h at 25° C. (Beckman L8-70M ultracentrifuge, Beckman Coulter, Fullerton, Calif.), followed by removal of the supernatant; the pelleted nanospheres were then washed twice with water, and re-suspended with gentle agitation in 1 mL of water at 25° C. Then, the volume of the re-suspended pellets was increased to 3 mL by the addition of water, and finally, the solutions were again filter-sterilized (0.22 μm).

Example 25. Preparation of Radio-Opaque Polymer and Nanosphere-Solute Formulations The Procedure of Example 24 was followed using the triblock copolymer prepared from PEG and oligo (I$_2$DTR-SA) to obtain radio-opaque polymers, and subsequently, radio-opaque nanospheres.

Examples 26-27. Preparation of Poly(Ethylene Glycol)-Block-Oligo-(DTR Suberate)-Block-Poly(Ethylene Glycol) Self-Assembling Nano Spheres Nomenclature:

The family of ABA triblock copolymers, poly(ethylene glycol)-block-oligo-(DTR suberate)-block-poly(ethylene glycol), are abbreviated as follows: the symmetrical PEG A-blocks are abbreviated as either 2K or 5K, meaning they have a molecular weight of 2000 or 5000 g/mol, respectively; the oligo B-blocks (suberic acid ester (SA) of desaminotyrosyl tyrosine alkyl ester (DTR)) are distinguished by their pendent ester R groups, where E is Ethyl, B=n-butyl, O=n-octyl, or Bn=benzyl. For example, the triblock oligomer PEG5K-b-oligo(desaminotyrosyl-tyrosine ethyl ester suberate)-b-PEG5K is abbreviated as 5K/DTE-SA.

Synthesis Procedure:

The triblock copolymers were synthesized in a one-pot reaction at 20° C. using in-situ carbodi-imide coupling of the PEG and oligo (DTR-SA), as disclosed in Nardin et al., Langmuir, vol. 20, 11721-25 (2004), the disclosure of which is incorporated herein by reference. To confirm that this method produced ABA triblock copolymers rather than random block copolymers, a two-step synthesis preparation was also performed in which the oligo (DTO-SA) B-block was prepared by a DIPC and DMPTS-catalyzed reaction of DTO and suberic acid. After being quenched with CTAB and water, this oligomer was isolated by precipitation, purified, and characterized.

In a separate reaction, oligo (DTO-SA) was reacted with monomethoxyterminated PEG (MeO-PEG-OH) under the same coupling conditions.

Block Copolymer Physical Characterization:

Molecular weights (Mn and $M_w$) were determined by gel permeation chromatography. The Mn values for the 2K PEG-containing triblocks fall within a narrow range between 10,300 and 11,500 g/mol. The Mn values for the 5K PEG-containing triblocks fall within a narrow range between 15,200 and 15,700 g/mol. These results are consistent with the difference in the copolymer molecular weights being dependent upon the PEG blocks in each triblock copolymers. In addition, $^1$H NMR studies support the accuracy of the molecular weights determined by GPC. The ratios of inte-grated peak areas for DTR-SA and PEG blocks provide the number of (DTR-SA) repeat units in the triblocks (data not shown), and using the known DTR-SA monomer and PEG molecular weights, give copolymers molecular weights that are in close agreement with the GPC molecular weights values.

The molecular weights for the 5K/DTO-SA triblock prepared by the two-step reaction process are M, −15300 g/mol and $M_w$ 25300 g/mol. The NMR spectra for the 5K/DTO-SA triblock products prepared by one-step and two-step procedures are identical. Similar comparisons of the other triblocks (not shown) consistently demonstrate the equivalence of the products by the one and two-step reactions.

The glass transition temperatures, $T_g$, of the hydrophobic oligo (DTR-SA) blocks are all greater than 0° C. and decrease as the lengths of the pendent R groups increase. Increasing the molecular weight of pure PEG homopolymer from 2000 to 5000 g/mol increases the melting point, Tm, from 53° C. to 63° C. In the triblock copolymers 2K/DTO-SA and 5K/DTO-SA, the increase in PEG molecular weights from 2000 to 5000 g/mol causes a similar increase in Tm, from 49° C. to 54° C. In all cases, the melting points of the copolymers are lower than the melting points of the corresponding pure PEG blocks, suggesting that the DTR-SA units reduces the degree of PEG crystallinity. Similarly, the difference between the $T_g$ values of −33° C. for all the triblocks and that of PEG homopolymer (−40° C.) can be attributed to a mixed phase morphology in the triblocks.

Nanosphere Preparation:

Self-assembly of the copolymers into nanospheres was induced by drop-wise addition of 100 mg/mL triblock oligomer in THF solution into deionized water under mild agitation to a final oligomer concentration of 4 mg/mL. The resulting turbid aqueous dispersions were filtered sequentially through 0.45 [tin, 0.22 pm and 0.1 pm size PVDF syringe filters (Millipore, Bedford, Mass.) and the clear filtrates were used for all physical characterizations. The hydrodynamic diameters of the nano spheres were determined by dynamic light scattering (PSS Nicomp Particle Sizing Systems, Santa Barbara, Calif.) at 30° C. using cumulant analysis and the Stokes-Einstein equation, and were consistent with particles sizes measured by electron microscopy as disclosed in Nardin et al., *Langmuir*, vol. 20, 11721-25 (2004).

Purified nanospheres were isolated by ultracentrifugation of 12.25 mL nanosphere solutions at 65,000 rpm (290,000× g) for 2.5 hours at 25° C. (Beckman L8-70M ultracentrifuge, Beckman Coulter, Fullerton, Calif.). Following removal of the supernatant, the pelleted nano spheres were washed twice with water and resuspended with gentle agitation in 1 mL of water at 25° C. The volume of the resuspended pellets was then increased to 12.25 mL by the addition of water and the solutions were filter sterilized.

Nano Sphere Characterization:

All of the triblock copolymers described here self-assemble spontaneously into nanospheres when added slowly to aqueous solution. The hydro-dynamic diameters of the nanospheres fall into two groups of about 46 nm and 70 nm, depending upon whether they contain 2K or 5K PEG blocks, respectively, and not upon the particular pendent R groups. The size distributions of 5K/DTO-SA nanospheres before and after ultracentrifugation are 62.9±31.3 nm and 60.6±25.9 nm, respectively, indicating that neither the presence of residual co-solvent in the nano sphere preparation nor ultracentrifugation have a significant effect on nanosphere structures. Since the nanosphere self-assembly is driven by non-covalent interactions, the nanospheres disintegrate upon dilution below the critical aggregation concentration (CAC). However, the CAC of 0.26 μg/mL for 2K/DTO-SA triblock is significantly lower than previously published values for other self-assembling block oligomer systems.

The $T_g$'s of the nanospheres are 21° C. for all nanosphere compositions as determined by solution DSC. The presence of the hydrated PEG blocks appears to plasticize the glass transition of the hydrophobic DTR-SA core components, whose $T_g$'s are 21° C. or higher.

This family of triblock copolymers is designed to degrade into biocompatible compounds under physiological conditions. HPLC analysis reveals approximately 70% of DTE monomer is converted to the free acid, desaminotryo sine (DT) following incubation in the presence of rabbit liver esterase for 30 min. The 5K/DTO-SA nano-spheres appear stable when incubated in PBS at pH 7.4 and 37° C. for up to 6 months, when a white precipitate forms and filtration results in the loss of all structures detectable by DLS.

Example 28. Preparation of Poly(Ethylene Glycol)-Block-Oligo-(DTO Carbonate)-Block-Poly(Ethylene Glycol) Self-Assembling Nanospheres Synthesis Procedure:

A 0.5 L 3-necked flask equipped with a mechanical stirrer and pump was purged with $N_2$ for 15 min. PEG was added to the flask followed by TP (solid) and DCM. The mixture was stirred to obtain a clear solution (10-15 min). At this point, reaction mixture contains "activated PEG"-PEG-chloroformate and an excess of unreacted TP. DTO and DCM were placed in the bottle with screw cap, and the TP solution was added to the reaction mixture using FMI pump (over 1 h). After the addition was complete, 10 ml of DCM were added to the bottle and were added to the reaction mixture over 10 min using the pump. After addition was complete, a 150 mL aliquot was withdrawn, evaporated to dryness with air and diluted with 1 mL of THF, filtered, and the filtrate was analyzed by GPC to determine the molecular weight distribution. GPC chromatogram revealed a mixture of products and reacted monomers. After the GPC run was completed, addition of 100 mL $H_2O$ quenched the reaction.

Work-Up:

The entire reaction mixture was concentrated by evaporation to a thick syrup (ca. 10 mL total), which was then precipitated with 60 mL of 2-propanol (drop-wise addition) and allowed to settle. The product was obtained as yellow thick oil, and the solvents were decanted off. The precipitate was dried (under $N_2$) for 20 min, redissolved in 10 mL of methylene chloride and precipitated with 60 mL of 2-propanol. Step 3 was repeated 2 more times with: a) 50 mL of methanol:IPA=1:1; b) 50 mL methanol. The product (thick gum) was dried under a stream of nitrogen followed by vacuum drying.

Block Copolymer Physical Characterization:

The molecular weight of PEG5K-oligo DTO carbonate-PEG5K was determined to be Mn=39,102 and Mw=53,758 by gel permeation chromatography, GPC (PL-gel columns, pore size $10^5$ and $10^4$ A, Perkin-Elmer, Shelton, Conn.; Waters 410 RI detector) with 1 mL/min THF flow rate and polystyrene standards. $^1$H Nuclear Magnetic Resonance (NMR) spectra were obtained in DMSO at 400 MHz and indicated about 180 (DTO-carbonate) units relative to PEG, which was in agreement with the PEG5K-oligo DTO carbonate-PEG5K structure.

Nanosphere Preparation and Characterization:

Self-assembly of the oligomers into nanospheres was induced by drop-wise addition of 100 mg/mL triblock oligomer in THF solution into deionized water under mild agitation to a final oligomer concentration of 4 mg/mL. The resulting turbid aqueous dispersions were filtered sequentially through 0.45 μm, 0.22 ∞m and 0.1 μm size PVDF syringe filters (Millipore, Bedford, Mass.) and the clear filtrates were used for all physical characterizations. The hydrodynamic diameters of the nanospheres were determined by dynamic light scattering (PSS Nicomp Particle Sizing Systems, Santa Barbara, Calif.) at 30° C. using cumulative analysis and the Stokes-Einstein equation, which yielded the following results after filtration: 0.45 μm: 132.4±48.6 nm; 0.22 μm: 121.5±39.0 nm; and 0.1 μm: 111.9±32.0 nm. All of the triblock oligomers described here self-assemble spontaneously into nanospheres when added slowly to aqueous solution. The hydrodynamic diameter of the nanospheres is about 112 nm.

TABLES

TABLE 1

Stoichiometric amount of curcumin, PEG, DTE and pyridine used to fabricate the curcumin-derived cross-linked polymer tissue scaffolds.

| Composition | Monomers input g (mmol) | | | Pyridine ml (mmol) | Yield % |
|---|---|---|---|---|---|
| | Curcumin | PEG | DTE | | |
| 50CUR50PEG | 1.8 (5) | 5.0 (5) | N/A | 1.6 (20) | 69 |
| 75CUR25PEG | 2.8 (7.5) | 2.5 (2.5) | N/A | 1.6 (20) | 93 |
| 25CUR75PEG | 0.9 (2.5) | 7.5 (7.5) | N/A | 1.6 (20) | 58 |
| 25CUR25DTE50PEG | 1.0 (3) | 5.6 (6) | 1 (3) | 1.9 (24) | 55 |
| 25CUR50DTE25PEG | 1.0 (3) | 2.8 (3) | 2 (6) | 1.9 (24) | 75 |

TABLE 2

Molecular weight (Mw)*, poly-dispersities (PDS), theoretical and experimental curcumin loading, glass transition temperatures (Tg) and elastic moduli (E) of curcumin-derived cross-linked polymer tissue scaffolds.

| | Mw* (kDa) | PDI | Theoretical Curcumin Content mol % | Experimental Curcumin Content (mol %) | Deviation in Curcumin Content % | Tg (° C.) | E (kPa) |
|---|---|---|---|---|---|---|---|
| 25CUR50DTE25PEG | 87 | 1.6 | 25 | 22 | 12 | −11 | 46 ± 0.7 |
| 25CUR25DTE50PEG | 200 | 1.5 | 25 | 30 | 17 | −25 | 7 ± 1.3 |
| 25CUR25I$_2$DTE50PEG | 150 | 1.7 | 25 | 31 | 20 | Tm = 110 | 9 ± 2 |
| 25CUR75PEG | 188 | 1.3 | 25 | 31 | 20 | −30 ($T_m$ = 36) | — |
| 50CUR50PEG | 165 | 1.5 | 50 | 56 | 11 | −19 | 21 ± 3 |
| 75CUR25PEG | 71 | 2.1 | 75 | 78 | 4 | 2 | 100 ± 30 |

*Maximum molecular weight that can be reached before cross-linking

TABLE 3

Chemotherapy agents

| | | |
|---|---|---|
| 1,3-cis-Retinoic Acid | BCG | Dacarbazine |
| 2-CdA | BCNU | Dacogen |
| 2-Chlorodeoxyadenosine | Bendamustine | Dactinomycin |
| 5-Azacitidine | Bevacizumab | Darbepoetin Alfa |
| 5-Fluorouracil | Bexarotene | Dasatinib |
| 5-FU | BEXXAR ® | Daunomycin |
| 6-Mercaptopurine | Bicalutamide | Daunorubicin |
| 6-MP | BiCNU | Daunorubicin |
| 6-TG | Blenoxane ® | Liposomal |
| 6-Thioguanine | Bleomycin | DaunoXome ® |
| Abraxane | Bortezomib | Decadron |
| Accutane ® | Busulfan | Decitabine |
| Actinomycin-D | Busulfex ® | Delta-Cortef ® |
| Adriamycin ® | C225 | Deltasone ® |
| Adrucil ® | Calcium | Denileukin |
| Agrylin ® | Leucovorin | Diftitox |
| Ala-Cort ® | Campath ® | DepoCyt ™ |
| Aldesleukin | Camptosar ® | Dexamethasone |
| Alemtuzumab | Camptothecin-11 | Dexasone |
| ALIMTA | Capecitabine | Dexrazoxane |
| Alitretinoin | Carac ™ | DHAD |
| Alkaban-AQ ® | Carboplatin | DIC |
| Alkeran ® | Carmustine | Diodex |
| All-transretinoic Acid | Carmustine Wafer | Docetaxel |
| Alpha Interferon | Casodex ® | Doxil ® |
| Altretamine | CC-5013 | Doxorubicin |
| Amethopterin | CCI-779 | Doxorubicin |
| Amifostine | CCNU | Liposomal |
| Aminoglutethimide | CDDP | Droxia ™ |
| Anagrelide | CeeNU | DTIC |
| Anandron ® | Cerubidine ® | DTIC-Dome ® |
| Anastrozole | Cetuximab | Duralone ® |
| Arabinosylcytosine | Chlorambucil | Efudex ® |
| Ara-C | Cisplatin | Eligard ™ |
| Aranesp ® | Citrovorum Factor | Ellence ™ |
| Aredia ® | Cladribine | Eloxatin ™ |
| Arimidex ® | Cortisone | Elspar ® |
| Aromasin ® | Cosmegen ® | Emcyt ® |
| Arranon ® | CPT-11 | Epirubicin |
| Arsenic Trioxide | Cyclophosphamide | Epoetin Alfa |
| Asparaginase | Cytadren ® | Erbitux |
| ATRA Avastin ® | Cytarabine | Erlotinib |
| Azacitidine | Cytarabine | Erwinia |
| Etoposide | Liposomal | L-asparaginase |
| Etoposide | Cytosar-U ® | Estramustine |
| Phosphate | Cytoxan ® | Ethyol |
| Eulexin ® | Ibritumomab | Etopophos ® |
| Evista ® | Ibritumomab | Matulane ® |
| Exemestane | Tiuxetan | Maxidex |
| Fareston ® | Idamycin ® | Mechlorethamine |
| Faslodex ® | Idarubicin | Medralone ® |
| Femara ® | Ifex ® | Medrol ® |
| Filgrastim | IFN-alpha | Megace ® |
| Floxuridine | Ifosfamide | Megestrol |
| Fludara ® | IL-11 | Megestrol Acetate |

TABLE 3-continued

Chemotherapy agents

| | | |
|---|---|---|
| Fludarabine | IL-2 | Melphalan |
| Fluoroplex ® | Imatinib mesylate | Mercaptopurine |
| Fluorouracil | Imidazole | Mesna |
| Fluorouracil (cream) | Carboxamide | Mesnex ™ |
| Fluoxymesterone | Interferon alfa | Methotrexate |
| Flutamide | Interferon Alfa-2b | Methylprednisolone |
| Folinic Acid | (PEG Conjugate) | Meticorten ® |
| FUDR ® | Interleukin-2 | Mitomycin |
| Fulvestrant | Interleukin-11 | Mitomycin-C |
| G-CSF | Intron A ® | Mitoxantrone |
| Gefitinib | (interferon alfa-2b) | M-Prednisol ® |
| Gemcitabine | Iressa ® | MTC |
| Gemtuzumab | Irinotecan | MTX |
| ozogamicin | Isotretinoin | Mustargen ® |
| Gemzar | Ixabepilone | Mustine |
| Gleevec ™ | Ixempra ™ | Mutamycin ® |
| Gliadel ® Wafer | Kidrolase (t) | Myleran ® |
| GM-CSF | Lanacort ® | Mylocel ™ |
| Goserelin | Lapatinib | Mylotarg ® |
| Granulocyte-Colony | L-asparaginase | Navelbine ® |
| Stimulating Factor | LCR | Nelarabine |
| Granulocyte | Lenalidomide | Neosar ® |
| Macrophage | Letrozole | Neulasta ™ |
| Colony Stimulating | Leucovorin | Neumega ® |
| Factor | Leukeran | Neupogen ® |
| Halotestin ® | Leukine ™ | Nexavar ® |
| Herceptin ® | Leuprolide | Nilandron ® |
| Hexadrol Hexalen ® | Leurocristine | Nilutamide |
| Hexamethylmelamine | Leustatin ™ | Nipent ® |
| HMM | Liposomal | Nitrogen Mustard |
| Hycamtin ® | Ara-C | Novaldex ® |
| Hydrea ® | Liquid Pred ® | Novantrone ® |
| Hydrocort Acetate ® | Lomustine | Octreotide |
| Hydrocortisone | L-PAM | Octreotide acetate |
| Hydroxyurea | L-Sarcolysin | Oncospar ® |
| Paclitaxel | Lupron ® | Oncovin ® |
| Protein-bound | Lupron Depot ® | Ontak ® |
| Pamidronate | Solu-Cortef ® | Onxal ™ |
| Panitumumab | Solu-Medrol ® | Oprevelkin |
| Panretin ® | Sorafenib | Oraprad ® |
| Paraplatin ® | SPRYCEL ™ | Orasone ® |
| Pediapred ® | STI-571 | Oxaliplatin |
| PEG Interferon | Streptozocin | VCR |
| Pegaspargase | SU11248 | Vectibix ™ |
| Pegfilgrastim | Sunitinib | Velban ® |
| PEG-INTRON ™ | Sutent ® | Velcade ® |
| PEG-L-asparaginase | Tamoxifen | VePesid ® |
| PEMETREXED | Tarceva ® | Vesanoid ® |
| Pentostatin | Targretin ® | Viadur ™ |
| Phenylalanine Mustard | Taxol ® | Vidaza ® |
| Platinol ® | Taxotere ® | Vinblastine |
| Platinol-AQ ® | Temodar ® | Vinblastine Sulfate |
| Prednisolone | Temozolomide | Vincasar Pfs ® |
| Prednisone | Temsirolimus | Vincristine |
| Prelone ® | Teniposide | Vinorelbine |

TABLE 3-continued

| Chemotherapy agents | | |
|---|---|---|
| Procarbazine | TESPA | Vinorelbine tartrate |
| PROCRIT ® | Thalidomide | VLB |
| Proleukin ® | Thalomid ® | VM-26 |
| Prolifeprospan 20 with Carmustine Implant | TheraCys ® | Vorinostat |
| | Thioguanine | VP-16 |
| Purinethol ® | Thioguanine | Vumon ® |
| Raloxifene | Tabloid ® | Xeloda ® |
| Revlimid ® | Thiophosphoamide | Zanosar ® |
| Rheumatrex ® | Thioplex ® | Zevalin ™ |
| Riluzole | Thiotepa | Zinecard ® |
| Rituxan ® | TICE ® | Zoladex ® |
| Rituximab | Toposar ® | Zoledronic acid |
| Roferon-A ® | Topotecan | Zolinza |
| (Interferon Alfa-2a) | Toremifene | Zometa ® |
| Rubex ® | Torisel ® | |
| Rubidomycin hydrochloride | Tositumomab | |
| | Trastuzumab | |
| Sandostatin ® | Treanda ® | |
| Sandostatin LAR ® | Tretinoin | |
| Sargramostim | Trexall ™ | |
| | Trisenox ® | |
| | TSPA | |
| | TYKERB ® | |

What is claimed is:

1. A biocompatible cross-linked polymer tissue scaffold composition for filling a void in soft tissue, which composition comprises a cross-linked polycarbonate, wherein said polycarbonate comprises
one or more diphenol monomers comprising curcumin,
one or more diphenol monomers comprising desaminotyrosyl tyrosine alkyl esters, desaminotyrosyl tyrosine free acid, or a mixture of desaminotyrosyl tyrosine alkyl esters and desaminotyrosyl tyrosine free acid, and
one or more hydrophilic poly(alkylene glycol) monomers,
in a molar ratio of total diphenol monomers to hydrophilic poly(alkylene glycol) monomers between about 25:75 and about 75:25, wherein the molar ratio of monomeric units is selected to determine the rate at which said curcumin is released; and
wherein, when present, the molar fraction of diphenol monomers carrying free carboxylic acid groups is about 10% to about 50% and the cross-link density is between about 8% and about 45%.

2. The composition of claim 1, wherein the molar ratio of diphenol monomers to hydrophilic monomers is between about 50:50 and about 75:25.

3. The composition of claim 1, wherein the mole fraction of desaminotyrosyl tyrosine alkyl esters, desaminotyrosyl tyrosine free acid, or a mixture of desaminotyrosyl tyrosine alkyl esters and desaminotyrosyl tyrosine free acid, is between about 10% and about 80% based on the total diphenol monomers.

4. The composition of claim 1, wherein said hydrophilic poly(alkylene glycol) monomers comprise poly(ethylene glycol)s.

5. The composition of claim 1, wherein said desaminotyrosyl tyrosine alkyl ester monomers, desaminotyrosyl tyrosine free acid monomers, or mixture of desaminotyrosyl tyrosine alkyl ester and desaminotyrosyl tyrosine free acid monomers, have iodine-substituted aromatic rings, which are present in an amount effective to render said cross-linked polymer tissue scaffold radio-opaque.

6. The composition of claim 1, wherein said composition further comprises a pharmaceutically active agent loaded into the cross-linked polymer tissue scaffold.

7. The composition of claim 6, wherein said pharmaceutically active agent is an anti-tumor drug.

8. The composition of claim 7, wherein said anti-tumor drug is tamoxifen.

9. The composition of claim 1, characterized in that said polymer is cross-linked with a dihydrazide to form an angiogenic composition.

10. The composition of claim 1, wherein said cross-linked polymer is in the form of macrobeads having a diameter of about 501 micrometers to about 5000 micrometers.

11. A method of treating a cavity formed by surgically removing soft tissue of a subject, said method comprising:
forming a biocompatible cross-linked polymer tissue scaffold composition to a size and shape that essentially fills said cavity;
inserting into said cavity said biocompatible cross-linked polymer tissue scaffold composition;
wherein said polymer comprises
one or more diphenol monomers comprising curcumin,
one or more diphenol monomers comprising desaminotyrosyl tyrosine alkyl esters, desaminotyrosyl tyrosine free acid, or a mixture of desaminotyrosyl tyrosine alkyl esters and desaminotyrosyl tyrosine free acid, and
one or more hydrophilic poly(alkylene glycol) monomers,
in a molar ratio of total diphenol monomers to hydrophilic monomers between about 25:75 and about 75:25, wherein the molar ratio of monomeric units is selected to determine the rate at which said curcumin is released, and wherein said composition is a hydrogel having essentially the same moisture content as tissue surrounding said cavity; and
closing said surgical cavity.

12. The method of claim 11, wherein said cavity is a lumpectomy cavity formed by surgically removing a breast cancer tumor.

13. The method of claim 12, wherein said composition further comprises an anti-tumor drug loaded into the cross-linked polymer tissue scaffold, wherein the anti-tumor drug is effective to prevent the growth or metastasis of any residual tumor cells.

14. The method of claim 12, wherein the desaminotyrosyl tyrosine alkyl ester monomers, desaminotyrosyl tyrosine free acid monomer, or mixture of desaminotyrosyl tyrosine alkyl ester and desaminotyrosyl tyrosine free acid monomers, have iodine-substituted aromatic rings, which are present in an amount effective to render said cross-linked polymer tissue scaffold sufficiently radio-opaque to render the scaffold x-ray visible and thereby define the borders of said cavity on an x-ray image, and said method further comprises the step of irradiating the cavity within said borders with therapeutic breast tumor radiation.

15. The method of claim 14, wherein the iodine-substituted diphenols comprise aromatic ring di-iodinated desaminotyrosyl tyrosine alkyl esters.

16. A method of targeting a lumpectomy cavity for radiation therapy, comprising:
removing a breast tumor by lumpectomy, thereby creating a lumpectomy cavity;
filling said lumpectomy cavity with a biocompatible cross-linked polymer tissue scaffold composition comprising a cross-linked copolymer, wherein said copolymer comprises
one or more diphenol monomers comprising curcumin,
one or more diphenol monomers comprising aromatic-ring di-iodinated desamino-tyrosyl tyrosine alkyl esters, aromatic-ring di-iodinated desaminotyrosyl tyrosine free acid, or a mixture of aromatic-ring di-iodinated desaminotyrosyl tyrosine alkyl esters and aromatic-ring di-iodinated desaminotyrosyl tyrosine free acid, and one or more hydrophilic poly(alkylene glycol) monomers, in a molar ratio of total diphenol monomers to hydrophilic monomers between about 25:75 and about 75:25, wherein said di-iodinated aromatic rings are present in an amount effective to render the cross-linked polymer tissue scaffold radio-opaque, the molar ratio of monomeric units is selected to determine the rate at which said curcumin is released, and said composition is a hydrogel having essentially the same moisture content of tissue surrounding said cavity;

imaging the cavity; and irradiating the imaged cavity at the boundaries of said imaged composition.

17. The biocompatible cross-linked polymer tissue scaffold composition of claim 1, wherein said copolymer is a terpolymer comprising:
   a) curcumin-containing monomers cross-linked via the curcumin enolic hydroxyl group;
   b) desaminotyrosyl tyrosine alkyl ester-containing monomers, desaminotyrosyl tyrosine free acid-containing monomer, or a mixture of desaminotyrosyl tyrosine alkyl ester- and desaminotyrosyl tyrosine free acid-containing monomers, optionally iodinated in the aromatic rings; and
   c) poly(alkylene glycol)-containing monomers;
   in a molar ratio a):b):c) of about 25-50: 25-50:25-50.

18. The biocompatible cross-linked polymer tissue scaffold composition of claim 17, wherein said terpolymer comprises the structure:

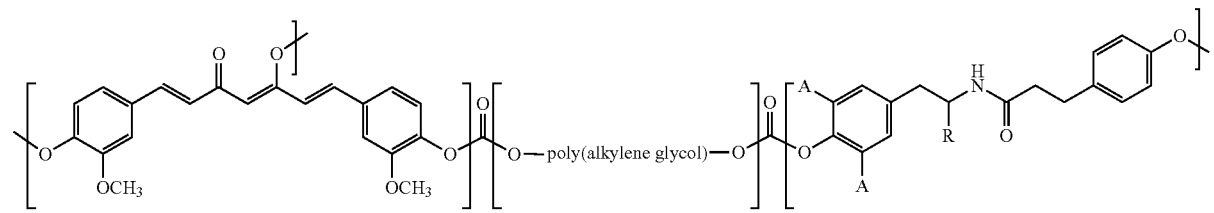

wherein the A groups are independently hydrogen or iodine, and the R group is CO2-alkyl, $CO_2H$ or a mixture of $CO_2$-alkyl and $CO_2H$.

19. The biocompatible cross-linked polymer tissue scaffold composition of claim 1, comprising the structure:

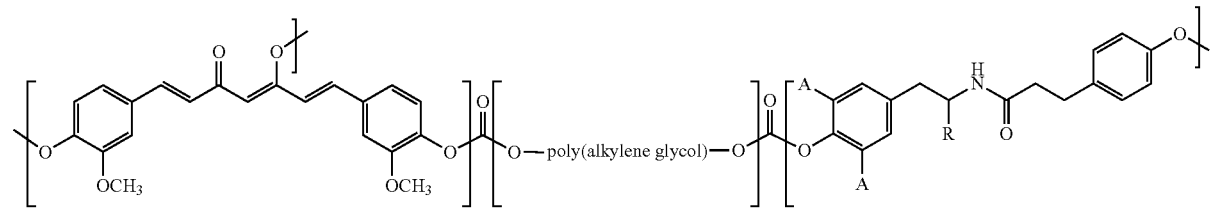

wherein the A groups are independently hydrogen or iodine, and the R group is CO2-alkyl, $CO_2H$ or a mixture of $CO_2$-alkyl and $CO_2H$.

20. The biocompatible cross-linked polymer tissue scaffold composition of claim 1, wherein said diphenol monomers comprising curcumin are cross-linked via the curcumin enolic hydroxyl group.

21. The biocompatible cross-linked polymer tissue scaffold composition of claim 1, wherein, when present, the molar fraction of diphenol monomers carrying free carboxylic acid groups is about 10% to about 40% and the cross-link density is between about 8% and about 35%.

* * * * *